United States Patent
Nakamura

(10) Patent No.: US 10,230,883 B2
(45) Date of Patent: Mar. 12, 2019

(54) IMAGING DEVICE, METHOD FOR CONTROLLING IMAGING DEVICE, AND CONTROL PROGRAM

(71) Applicant: JVC KENWOOD Corporation, Yokohama-shi, Kanagawa (JP)

(72) Inventor: Isao Nakamura, Yokohama (JP)

(73) Assignee: JVC KENWOOD CORPORATION, Yokohama-Shi, Kanagawa (JP)

( * ) Notice: Subject to any disclaimer, the term of this patent is extended or adjusted under 35 U.S.C. 154(b) by 133 days.

(21) Appl. No.: 15/390,218

(22) Filed: Dec. 23, 2016

(65) Prior Publication Data

US 2017/0111562 A1    Apr. 20, 2017

Related U.S. Application Data

(63) Continuation of application No. PCT/JP2015/072862, filed on Aug. 12, 2015.

(30) Foreign Application Priority Data

Sep. 2, 2014 (JP) .................... 2014-178003

(51) Int. Cl.
| | |
|---|---|
| *G01N 21/35* | (2014.01) |
| *G01N 21/359* | (2014.01) |
| *H04N 5/33* | (2006.01) |
| *H04N 5/232* | (2006.01) |
| *H04N 5/353* | (2011.01) |

(Continued)

(52) U.S. Cl.
CPC ........... *H04N 5/232* (2013.01); *G01N 21/35* (2013.01); *H04N 5/2256* (2013.01); *H04N 5/23229* (2013.01); *H04N 5/23245* (2013.01); *H04N 5/33* (2013.01); *H04N 5/353* (2013.01);

(Continued)

(58) Field of Classification Search
CPC .... G01J 3/108; G01J 3/0294; G01J 2003/045; G01N 21/35
See application file for complete search history.

(56) References Cited

U.S. PATENT DOCUMENTS

| | | | | |
|---|---|---|---|---|
| 4,959,710 A | * | 9/1990 | Uehara ................ | A61B 1/0638 348/E5.038 |
| 4,974,076 A | * | 11/1990 | Nakamura ............... | A61B 1/05 348/71 |

FOREIGN PATENT DOCUMENTS

JP    2011050049 A    3/2011

OTHER PUBLICATIONS

ISA 237 Form dated Nov. 2, 2016 corresponding to International application No. PCT/JP2015/072862.

* cited by examiner

*Primary Examiner* — Sathyanaraya V Perungavoor
*Assistant Examiner* — Clifford Hilaire
(74) *Attorney, Agent, or Firm* — Nath, Goldberg & Meyer; Jerald L. Meyer; Stanley N. Protigal

(57) ABSTRACT

An imaging unit images an object in a state where first to third infrared lights are each selectively and sequentially projected so as to generate first to third frames. An electronic shutter controller controls a period and timing in which the imaging unit is exposed such that an interval between a first timing, which is the middle point of the period in which the imaging unit is exposed in the state where the second infrared light is projected, and a second timing, which is the middle point of the period in which the imaging unit is exposed in the state where the first or third infrared light is projected, is set shorter than an interval between the first timing and a third timing, which is the middle point of the one frame period of the first or third frame.

4 Claims, 27 Drawing Sheets

(51) Int. Cl.
 *H04N 9/07* (2006.01)
 *H04N 5/225* (2006.01)
 *H04N 5/355* (2011.01)
 *H04N 9/04* (2006.01)
(52) U.S. Cl.
 CPC ......... *H04N 5/35581* (2013.01); *H04N 9/045* (2013.01); *H04N 9/07* (2013.01)

FIG. 13
(a) 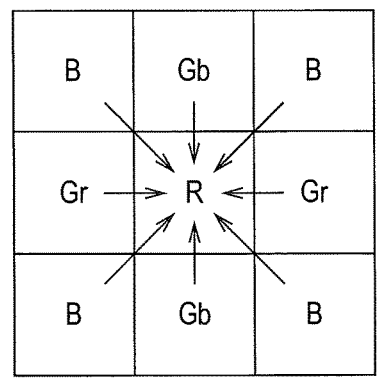
(b) 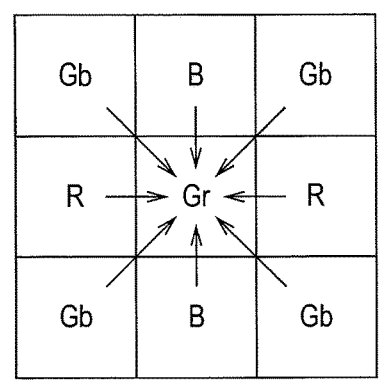
(c) 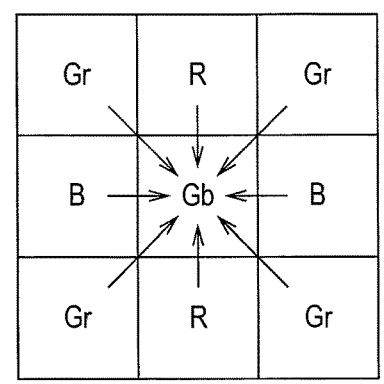
(d) 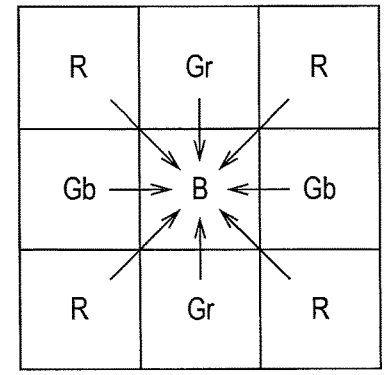

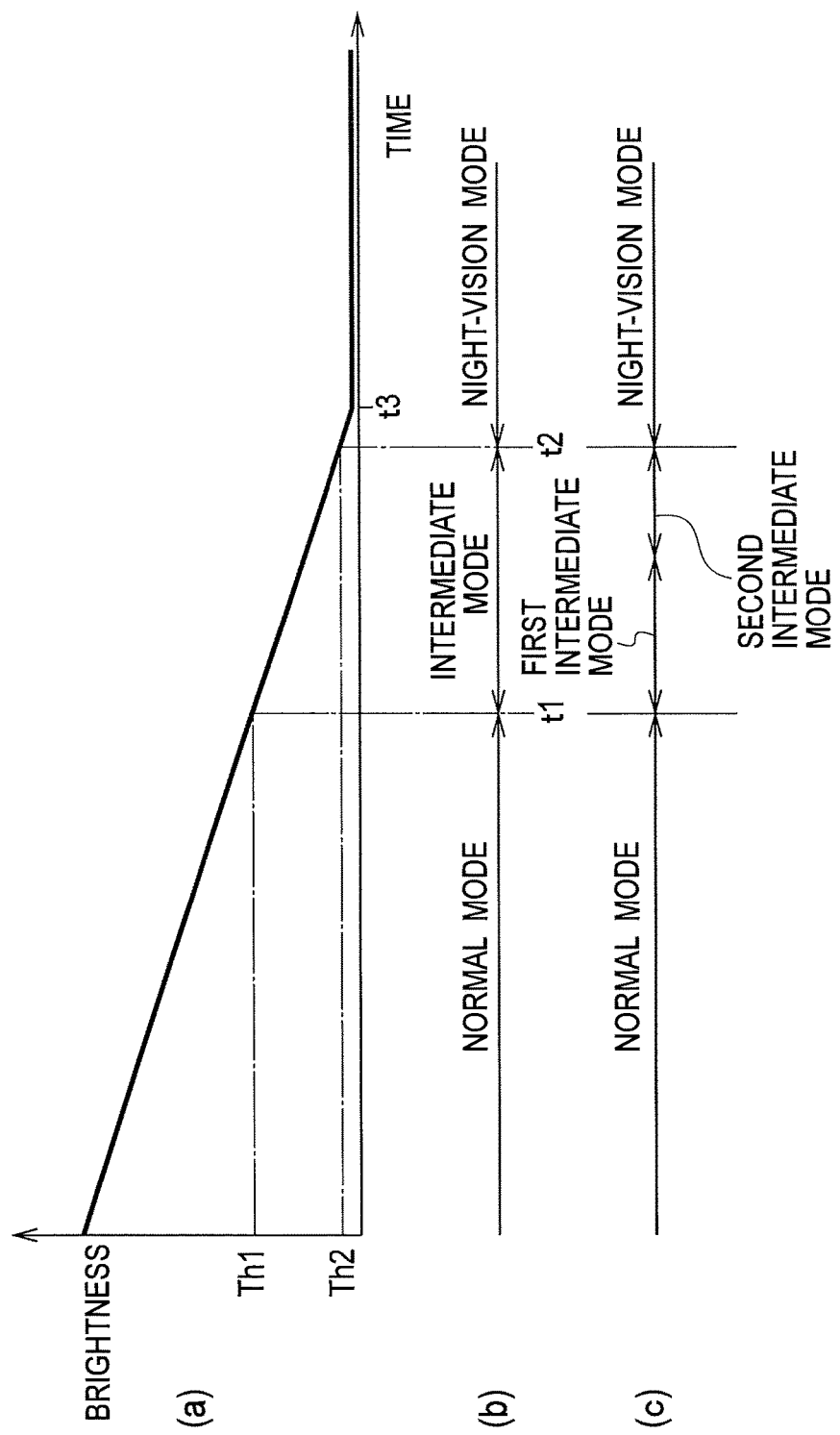

FIG. 20

| | INFRARED PROJECTOR 9 | PRE-SIGNAL PROCESSING UNIT 52 | | | DEMOSAICING UNIT 54 |
|---|---|---|---|---|---|
| | | SURROUNDING PIXEL ADDING UNIT 521 | SAME-POSITION PIXEL ADDING UNIT 522 | SYNTHESIZING UNIT 523 | |
| NORMAL MODE | OFF | INACTIVATED | INACTIVATED | INACTIVATED | ACTIVATED |
| FIRST INTERMEDIATE MODE | ON | INACTIVATED | ACTIVATED | ACTIVATED | |
| SECOND INTERMEDIATE MODE | ON | INACTIVATED | INACTIVATED | ACTIVATED | |
| FIRST NIGHT-VISION MODE | ON | ACTIVATED | ACTIVATED | ACTIVATED | |
| SECOND NIGHT-VISION MODE | ON | ACTIVATED | INACTIVATED | ACTIVATED | |

IMAGING DEVICE, METHOD FOR CONTROLLING IMAGING DEVICE, AND CONTROL PROGRAM

CROSS REFERENCE TO RELATED APPLICATION

This application is a Continuation of PCT Application No. PCT/JP2015/072862, filed on Aug. 12, 2015, and claims the priority of Japanese Patent Application No. 2014-178003, filed on Sep. 2, 2014, the entire contents of both of which are incorporated herein by reference.

BACKGROUND

The present disclosure relates to an imaging device, a method for controlling an imaging device, and a control program.

There is known a method for imaging an object under the condition that almost no visible light is available, such as during nighttime, by radiating infrared light onto the object from an infrared projector and imaging infrared light reflected by the object. This imaging method is effective in a case where lighting fixtures for radiating visible light cannot be used.

However, since an image obtained by imaging the object by this method is a monochromatic image, it is difficult to identify the object from the monochromatic image depending on circumstances. If a color image can be captured even under the condition that no visible light is available, the performance of identifying the object can be improved. For example, it is expected that surveillance cameras can capture color images under the condition that no visible light is available in order to improve performance for identifying objects.

Japanese Unexamined Patent Application Publication No. 2011-050049 (Patent Document 1) describes an imaging device capable of capturing color images under the condition that no visible light is available. The imaging device described in Patent Document 1 uses an infrared projector. Incorporating the technique described in Patent Document 1 into a surveillance camera can capture a color image of an object so as to improve the identification of the object.

SUMMARY

The imaging device, using the infrared projector, may cause variations in color when imaging a moving object by radiating infrared light onto the object.

A first aspect of the embodiments provides an imaging device including: a projection controller configured to control an infrared projector to selectively and sequentially project a first infrared light having a first wavelength assigned to a first color of red, green, and blue, a second infrared light having a second wavelength assigned to a second color of red, green, and blue, and a third infrared light having a third wavelength assigned to a third color of red, green, and blue; an imaging unit configured to image an object in a state where the first infrared light is projected in at least part of one frame period so as to generate a first frame based on a first imaging signal, image the object in a state where the second infrared light is projected in at least part of the one frame period so as to generate a second frame based on a second imaging signal, and image the object in a state where the third infrared light is projected in at least part of the one frame period so as to generate a third frame based on a third imaging signal; an electronic shutter controller configured to control a function of an electronic shutter in the imaging unit; and an image processing unit configured to synthesize the first to third frames to generate a frame of an image signal, wherein the electronic shutter controller controls a period and timing in which the imaging unit is exposed such that an interval between a first timing and a second timing is set shorter than an interval between the first timing and a third timing, the first timing being a middle point of a period in which the imaging unit is exposed in the state where the second infrared light is projected, the second timing being a middle point of a period in which the imaging unit is exposed in the state where the first or third infrared light is projected, and the third timing being a middle point of the one frame period of the first or third frame.

A second aspect of the embodiments provides a method for controlling an imaging device, including: a first step of imaging an object by an imaging unit in a state where a first infrared light having a first wavelength assigned to a first color of red, green, and blue is projected in at least part of one frame period so as to generate a first frame based on a first imaging signal; a second step, implemented after the first step, of imaging the object by the imaging unit in a state where a second infrared light having a second wavelength assigned to a second color of red, green, and blue is projected in at least part of the one frame period so as to generate a second frame based on a second imaging signal; a third step, implemented after the second step, of imaging the object by the imaging unit in a state where a third infrared light having a third wavelength assigned to a third color of red, green, and blue is projected in at least part of the one frame period so as to generate a third frame based on a third imaging signal; and a fourth step of synthesizing the first to third frames to generate a frame of an image signal, wherein, in the first to third steps, a period and timing in which the imaging unit is exposed in a state where the first to third infrared lights are each projected, are determined by use of a function of an electronic shutter in the imaging unit, and an interval between a first timing and a second timing is set shorter than an interval between the first timing and a third timing, the first timing being a middle point of a period in which the imaging unit is exposed in the state where the second infrared light is projected, the second timing being a middle point of a period in which the imaging unit is exposed in the state where the first or third infrared light is projected, and the third timing being a middle point of the one frame period of the first or third frame.

A third aspect of the embodiments provides a control program of an imaging device executed by a computer and stored in a non-transitory storage medium to implement the following steps, including: a first step of controlling an infrared projector to project a first infrared light having a first wavelength assigned to a first color of red, green, and blue; a second step of imaging an object by an imaging unit in a state where the first infrared light is projected in at least part of one frame period so as to generate a first frame based on a first imaging signal; a third step, continued from the first step, of controlling the infrared projector to project a second infrared light having a second wavelength assigned to a second color of red, green, and blue; a fourth step of imaging the object by the imaging unit in a state where the second infrared light is projected in at least part of the one frame period so as to generate a second frame based on a second imaging signal; a fifth step, continued from the third step, of controlling the infrared projector to project a third infrared light having a third wavelength assigned to a third color of red, green, and blue; a sixth step of imaging the object by the imaging unit in a state where the third infrared light is projected in at least part of the one frame period so as to generate a third frame based on a third imaging signal; and a seventh step of synthesizing the first to third frames to generate a frame of an image signal, wherein, in the second, fourth, and sixth steps, the control program implements processing to control a period and timing in which the imaging unit is exposed by use of a function of an electronic shutter in the imaging unit such that an interval between a first timing and a second timing is set shorter than an interval between the first timing and a third timing, the first timing being a middle point of a period in which the imaging unit is exposed in the state where the second infrared light is projected, the second timing being a middle point of a period in which the imaging unit is exposed in the state where the first or third infrared light is projected, and the third timing being a middle point of the one frame period of the first or third frame.

BRIEF DESCRIPTION OF THE DRAWINGS

FIG. 13 is a view for describing processing of adding surrounding pixels when the imaging device according to the embodiment is operating in the night-vision mode.

FIG. 19 is a view for describing an example of a mode switch in the imaging device according to the embodiment.

FIG. 20 is a view showing conditions of the respective members when the imaging device according to the embodiment is set to the respective modes.

DETAILED DESCRIPTION

Hereinafter, an imaging device, a method for controlling an imaging device, and a control program according to the embodiment will be described with reference to appended drawings.

<Configuration of Imaging Device>

First, the entire configuration of the imaging device according to the embodiment is described below with reference to FIG. 1. The imaging device according to the embodiment shown in FIG. 1 is capable of capturing images in three modes including a normal mode suitable for imaging in a state where sufficient visible light is present such as during the day, a night-vision mode suitable for imaging in a state where almost no visible light is present such as at night, and an intermediate mode suitable for imaging in a state where visible light is slightly present.

The intermediate mode is a first infrared light projecting mode for imaging while projecting infrared light under the condition that the amount of visible light is small. The night-vision mode is a second infrared light projecting mode for imaging while projecting infrared light under the condition that the amount of visible light is smaller (almost no visible light is present).

The imaging device may include either the intermediate mode or the night-vision mode. The imaging device does not necessarily include the normal mode. The imaging device is only required to include an infrared light projecting mode for imaging while projecting infrared light.

Figure 1:
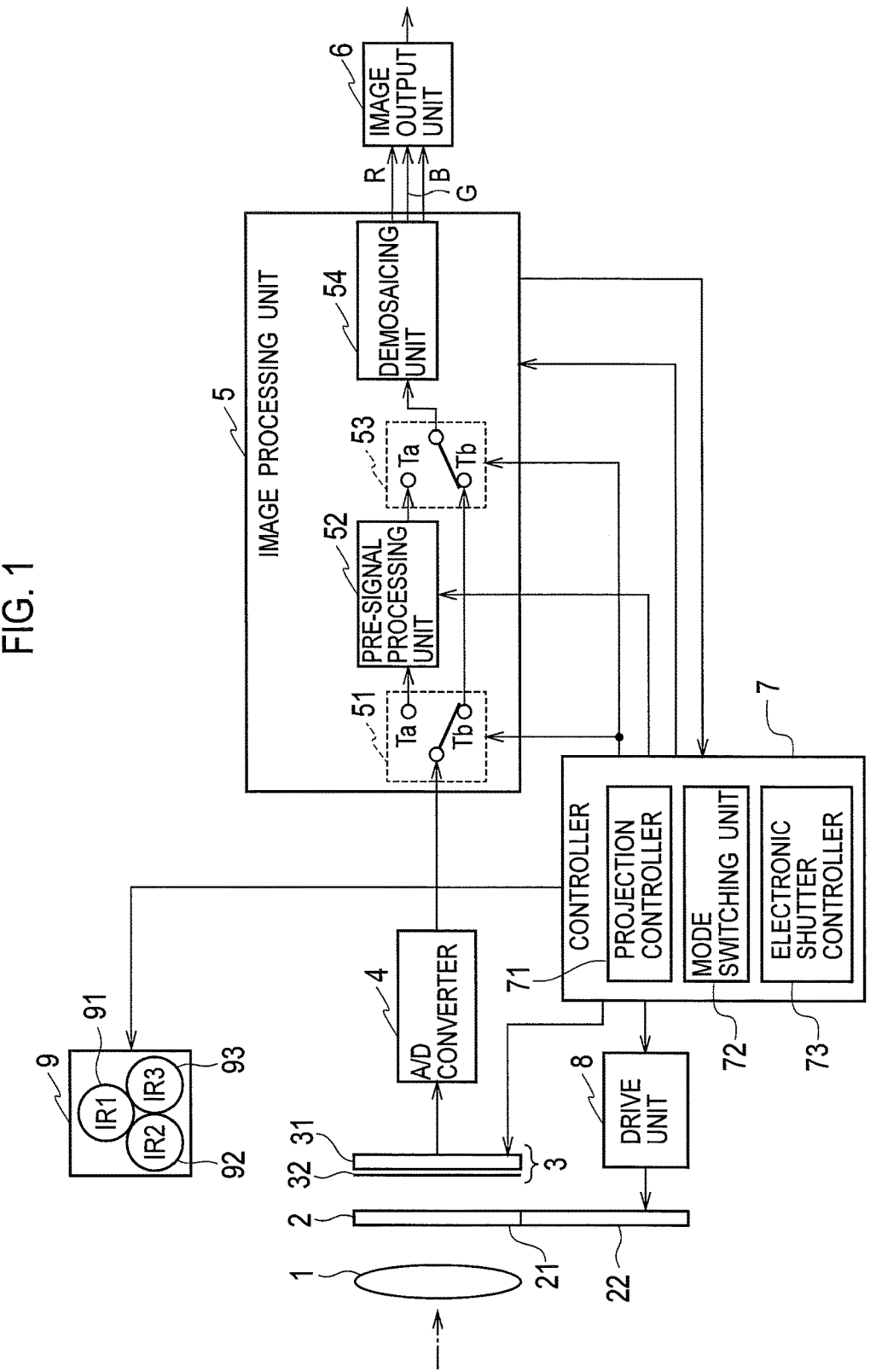
FIG. 1 is a block diagram showing an overall configuration of an imaging device according to at least one embodiment.

As shown in FIG. 1, a light indicated by the dash-dotted line reflected by an object is collected by an optical lens 1. Visible light enters the optical lens 1 under the condition that visible light is present sufficiently, and infrared light emitted from an infrared projector 9 described below and reflected by the object enters the optical lens 1 under the condition that almost no visible light is present.

In the state where visible light is slightly present, mixed light including both the visible light and the infrared light emitted from the infrared projector 9 and reflected by the object, enters the optical lens 1.

Although FIG. 1 shows only one optical lens 1 for reasons of simplification, the imaging device actually includes a plurality of optical lenses.

An optical filter 2 is interposed between the optical lens 1 and an imaging unit 3. The optical filter 2 includes two members; an infrared cut filter 21 and a dummy glass 22. The optical filter 2 is driven by a drive unit 8 in a manner such that the infrared cut filter 21 is inserted between the optical lens 1 and the imaging unit 3 or such that the dummy glass 22 is inserted between the optical lens 1 and the imaging unit 3.

The imaging unit 3 includes an imaging element 31 in which a plurality of light receiving elements (pixels) are arranged in both the horizontal direction and the vertical direction, and a color filter 32 in which filter elements of red (R), green (G), or blue (B) corresponding to the respective light receiving elements are arranged. The imaging element 31 may be either a charge coupled device (CCD) or a complementary metal oxide semiconductor (CMOS).

Figure 2:
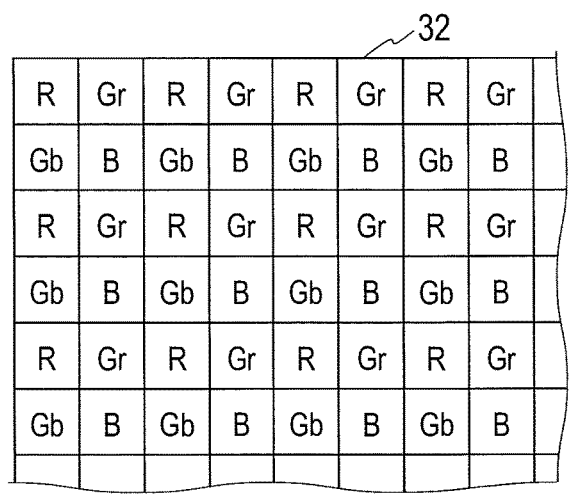
FIG. 2 is a view showing an example of an array of filter elements in a color filter used in the imaging device according to the embodiment.

In the color filter 32, for example, the filter elements of each of R, G, and B are arranged in a pattern called a Bayer array, as shown in FIG. 2. The Bayer array is an example of predetermined arrays of the filter elements of R, G, and B. In FIG. 2, each of the filter elements of G in each line held between the filter elements of R is indicated by Gr, and each of the filter elements of G held between the filter elements of B is indicated by Gb.

The Bayer array has a configuration in which the horizontal lines alternating the filter elements of R with the filter elements of Gr and the horizontal lines alternating the filter elements of B with the filter elements of Gb are aligned alternately with each other in the vertical direction.

Figure 3:
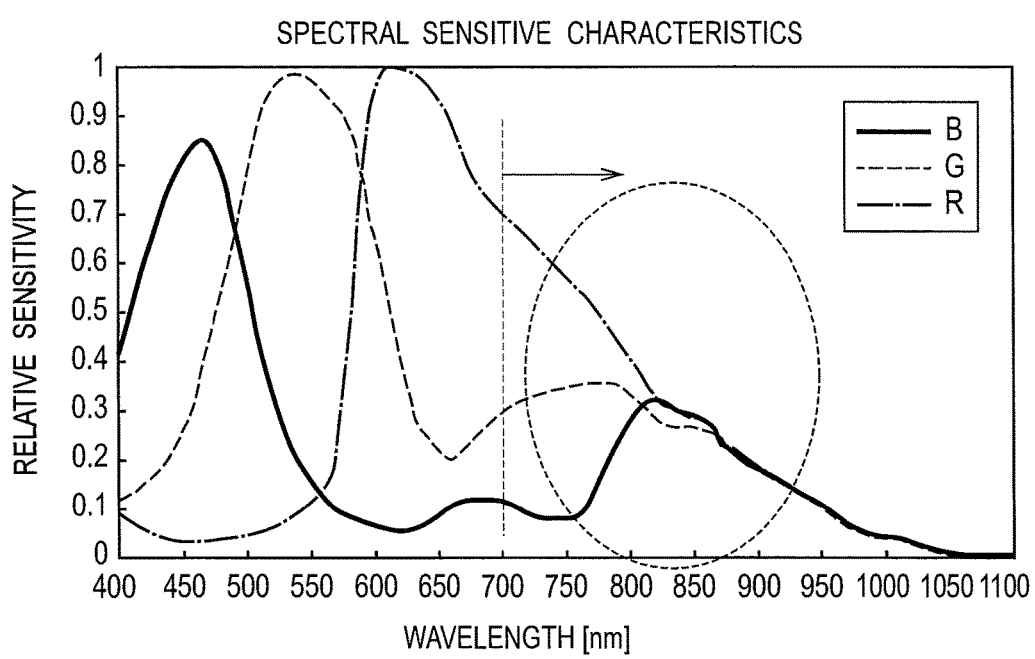
FIG. 3 is a characteristic diagram showing spectral sensitive characteristics of wavelengths and relative sensitivities of light of three primary colors in an imaging unit included in the imaging device according to the embodiment.

FIG. 3 shows spectral sensitive characteristics of wavelengths and relative sensitivities of R light, G light, and B light in the imaging unit 3. The maximum value of the relative sensitivities is normalized to 1. When the imaging device is operated in the normal mode, infrared light having a wavelength of 700 nm or greater is required to be blocked in order to capture fine color images with visible light.

The drive unit 8 is thus controlled by a controller 7 to drive the optical filter 2 in such a manner as to insert the infrared cut filter 21 between the optical lens 1 and the imaging unit 3.

As is apparent from FIG. 3, the imaging unit 3 shows the sensitivities in the area where the infrared light having the wavelength of 700 nm or greater is present. Therefore, when the imaging device is operated in the intermediate mode or in the night-vision mode, the drive unit 8 is controlled by the controller 7 to drive the optical filter 2 in such a manner as to remove the infrared cut filter 21 from between the optical lens 1 and the imaging unit 3 and insert the dummy glass 22 therebetween.

When the dummy glass 22 is inserted between the optical lens 1 and the imaging unit 3, the infrared light having the wavelength of 700 nm or greater is not blocked. Thus, the imaging device can obtain information of each of R, G and B by using the sensitivities in the oval region surrounded by the broken line in FIG. 3. The reason the dummy glass 22 is inserted is to conform the optical path length obtained when the dummy glass 22 is used to the optical path length obtained when the infrared cut filter 21 is used.

The infrared projector 9 includes projecting portions 91, 92, and 93 for projecting infrared light with wavelengths IR1, IR2, and IR3, respectively. In the case of the intermediate mode or the night-vision mode, a projection controller 71 in the controller 7 controls the projecting portions 91, 92, and 93 so as to selectively project the infrared light with the respective wavelengths IR1, IR2, and IR3 in a time division manner.

Figure 4:
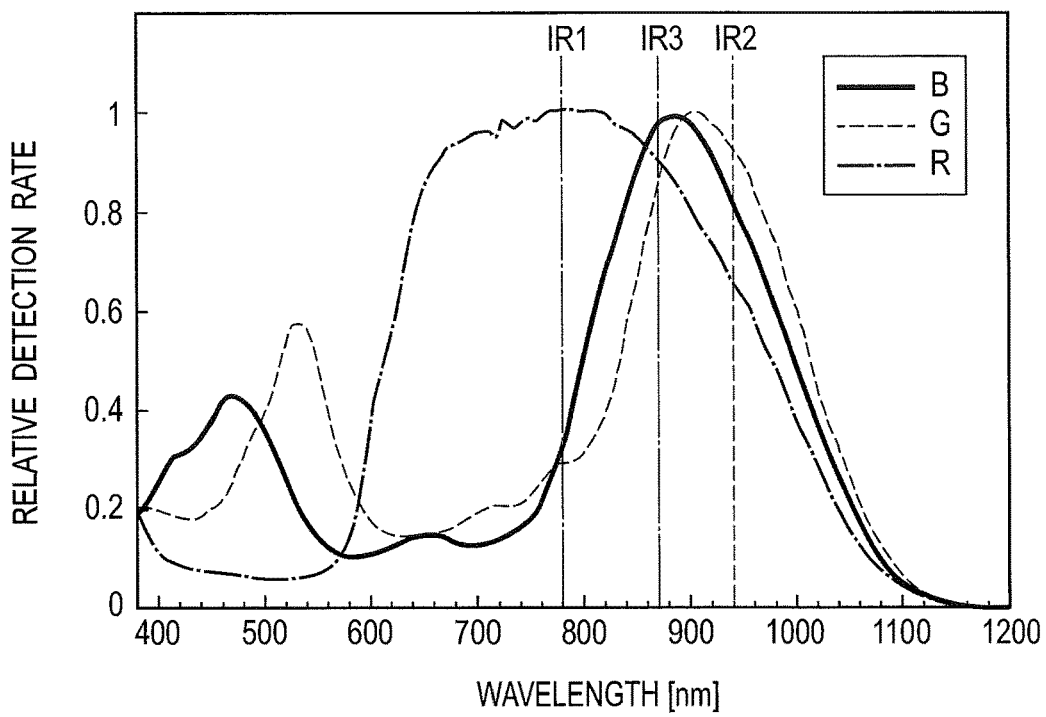
FIG. 4 is a characteristic diagram showing a relationship between wavelengths and relative detection rates when multiplying, by a light receiving sensitivity of silicon, a reflectance of light of each primary color obtained from a particular substance.

A silicon wafer is used in the imaging element 31. FIG. 4 shows a relationship between wavelengths and relative detection rates when a reflectance at each wavelength is multiplied by a light receiving sensitivity of silicon in a case where a material consisting of each of the colors R, G, and B is irradiated with white light. The maximum value of the relative detection rates in FIG. 4 is also normalized to 1.

For example, as shown in FIG. 4, in the infrared light area, the reflected light with the wavelength of 780 nm has a strong correlation with the reflected light of the material with color R, the reflected light with the wavelength of 870 nm has a strong correlation with the reflected light of the material with color B, and the reflected light with the wavelength of 940 nm has a strong correlation with the reflected light of the material with color G.

Thus, according to the present embodiment, the wavelengths IR1, IR2, and IR3 of infrared light projected from the projecting portions 91, 92, and 93 are set to 780 nm, 940 nm, and 870 nm, respectively. These values are examples for the wavelengths IR1, IR2, and IR3, and other wavelengths other than 780 nm, 940 nm, and 870 nm may also be employed.

The projecting portion 91 radiates the infrared light with the wavelength IR1 on an object, and an image signal obtained, in a manner such that light reflected by the object is captured, is assigned to an R signal. The projecting portion 93 radiates the infrared light with the wavelength IR2 on the object, and an image signal obtained, in a manner such that light reflected by the object is captured, is assigned to a G signal. The projecting portion 92 radiates the infrared light with the wavelength IR3 on the object, and an image signal obtained, in a manner such that light reflected by the object is captured, is assigned to a B signal.

Accordingly, in the intermediate mode or in the night-vision mode, a color similar to that obtained when the object is imaged in the normal mode in the state where visible light is present, can also be reproduced theoretically.

Alternatively, the wavelength IR1 of 780 nm may be assigned to the R light, the wavelength IR3 of 870 nm may be assigned to the G light, and the wavelength IR2 of 940 nm may be assigned to the B light, although in this case the color image would possess a color tone different from the actual color tone of the object. The wavelengths IR1, IR2, and IR3 may be assigned optionally to the R light, the G light, and the B light.

According to the present embodiment, the wavelengths IR1, IR2, and IR3 are assigned to the R light, the G light, and the B light, respectively, by which the color tone of the object can be reproduced most finely.

The controller 7 controls the imaging unit 3 and the components included in an image processing unit 5. An electronic shutter controller 73 included in the controller 7 controls functions of an electronic shutter in the imaging unit 3. Image signals of images captured by the imaging unit 3 are subjected to A/D conversion by an A/D converter 4, and are then input into the image processing unit 5. The imaging unit 3 and the A/D converter 4 may be integrated.

The controller 7 includes a mode switching unit 72 that switches between the normal mode, the intermediate mod, and the night-vision mode. The mode switching unit 72 switches the operations in the image processing unit 5 as appropriate to correspond to the normal mode, the intermediate mode, and the night-vision mode, as described below. The image processing unit 5 and the controller 7 may be integrated.

The image processing unit 5 includes switches 51 and 53, a pre-signal processing unit 52, and a demosaicing unit 54. The switches 51 and 53 may be physical switches or may be logical switches for switching the pre-signal processing unit 52 between an active state and an inactive state. The controller 7 receives an image signal output from the image processing unit 5 in order to detect the brightness of the image being captured.

Figure 5:
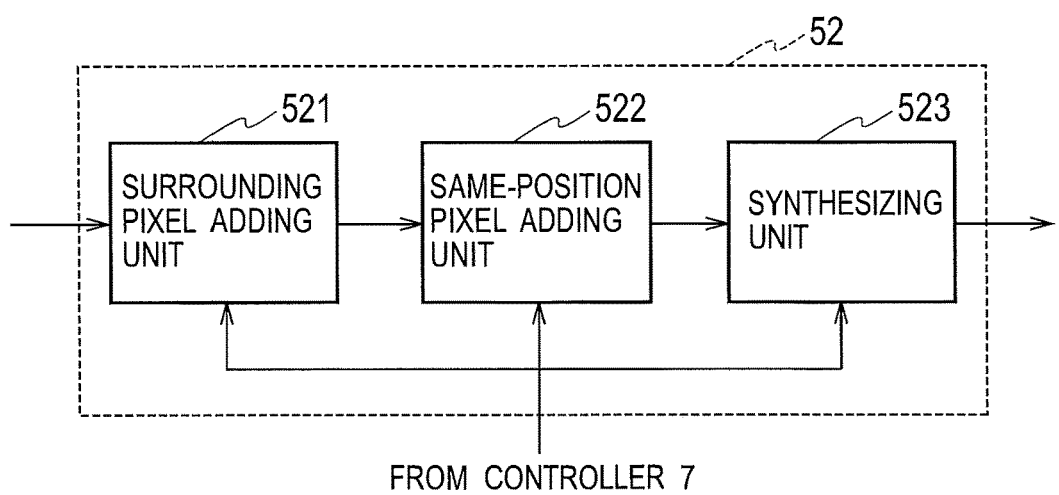
FIG. 5 is a block diagram showing a specific configuration example of a pre-signal processing unit 52 shown in FIG. 1.

As shown in FIG. 5, the pre-signal processing unit 52 includes a surrounding pixel adding unit 521, a same-position pixel adding unit 522, and a synthesizing unit 523.

The image processing unit 5 generates data for the respective three primary colors R, G, and B, and supplies the data to the image output unit 6. The image output unit 6 outputs the data for the three primary colors in a predetermined format to a display unit (not shown) or the like.

The image output unit 6 may directly output signals of the three primary colors R, G and B, or may convert the signals of the three primary colors R, G and B into luminance signals and color signals (or color difference signals) before outputting. The image output unit 6 may output composite image signals. The image output unit 6 may output digital image signals or output image signals converted into analog signals by a D/A converter.

Next, the operations of each of the normal mode, the intermediate mode, and the night-vision mode are described in more detail below.

<Normal Mode>

In the normal mode, the controller 7 directs the drive unit 8 to insert the infrared cut filter 21 between the optical lens 1 and the imaging unit 3. The projection controller 71 turns off the infrared projector 9 to stop projecting infrared light.

Image signals captured by the imaging unit 3 are converted into image data as digital signals by the A/D converter 4, and then input into the image processing unit 5. In the normal mode, the mode switching unit 72 connects the switches 51 and 53 to the respective terminals Tb.

Figure 6:
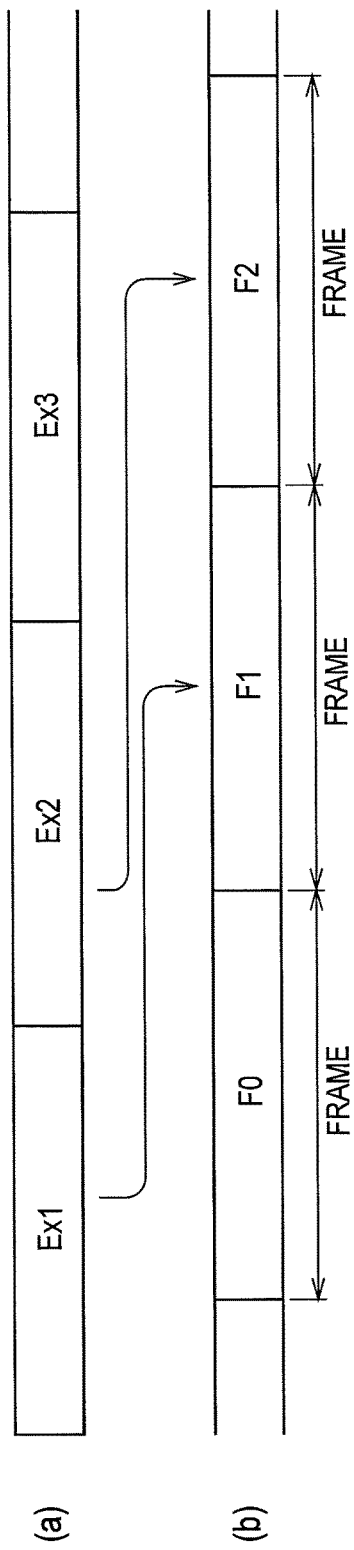
FIG. 6 is a view showing a relationship between exposures and frames of image signals when the imaging device according to the embodiment is operating in a normal mode.

Item (a) of FIG. 6 shows exposures Ex1, Ex2, Ex 3, etc., of the imaging unit 3. Although the actual exposure time varies depending on conditions such as shutter speed, each of the exposures Ex1, Ex2, Ex 3, etc., denotes the maximum exposure time. The shutter speed is determined depending on the control by the electronic shutter controller 73.

Item (b) of FIG. 6 shows the timing at which each of frames of the image signals is obtained. Frame F0 of the image signals is obtained based on an exposure (not shown) prior to the exposure Ex1 after a predetermined period of time. Frame F1 of the image signals is obtained based on the exposure Ex1 after a predetermined period of time. Frame F2 of the image signal is obtained based on the exposure Ex2 after a predetermined period of time. The same operations are repeated after the exposure Ex3. A frame frequency of the image signals is, for example, 30 frames per second.

The frame frequency of the image signals that may be determined as appropriate is that such as 30 frames per second or 60 frames per second in the NTSC format, and 25 frames per second or 50 frames per second in the PAL format. Alternatively, the frame frequency of the image signals may be 24 frames per second, which is used for movies.

The image data of each frame output from the A/D converter 4 is input into the demosaicing unit 54 via the switches 51 and 53. The demosaicing unit 54 subjects the image data of each input frame to demosaicing. The image processing unit 5 subjects the data to other types of image processing in addition to the demosaicing, and outputs the data of the three primary colors R, G and B.

Figure 7:
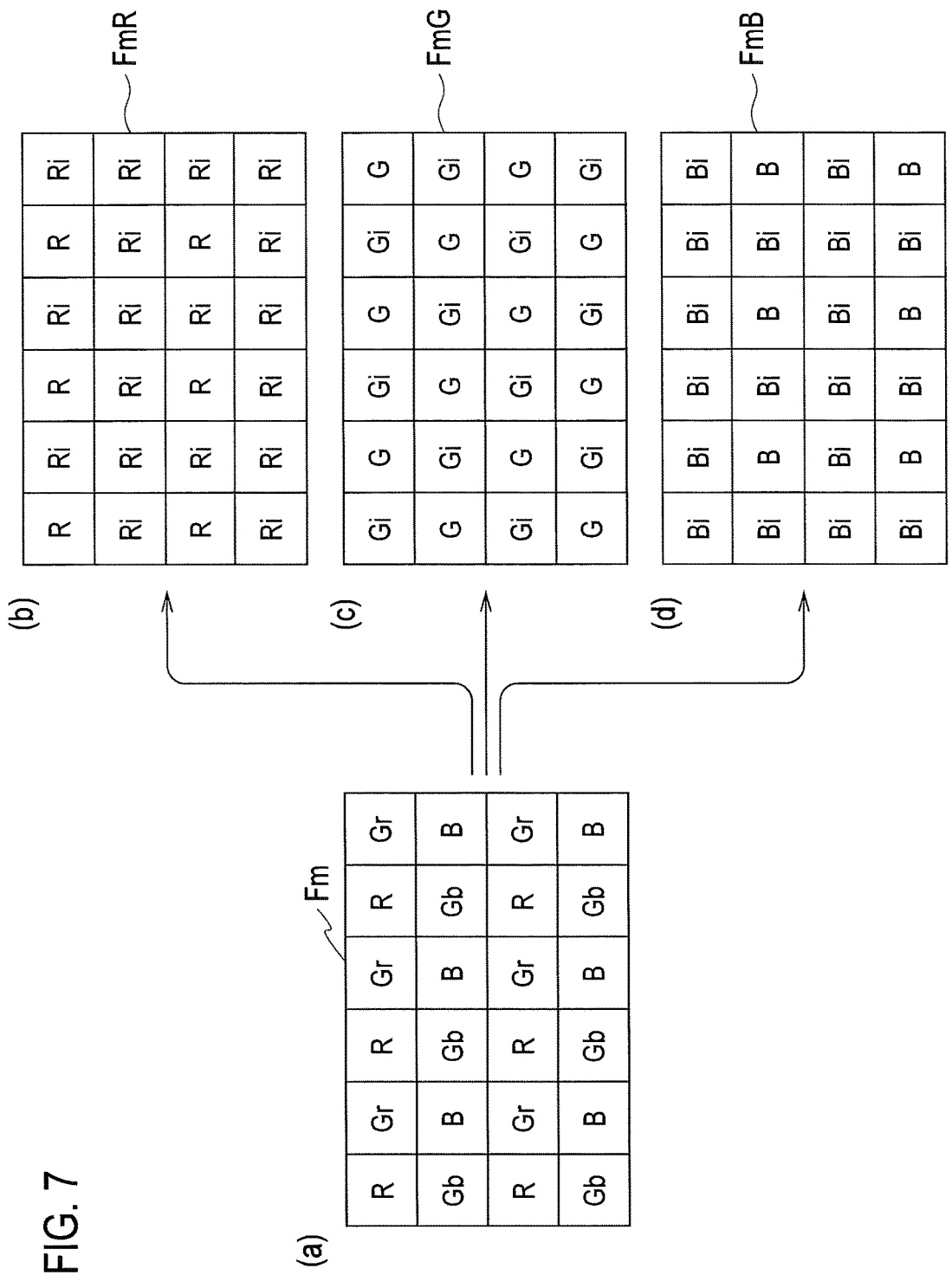
FIG. 7 is a view for describing demosaicing when the imaging device according to the embodiment is operating in the normal mode.

The demosaicing in the demosaicing unit 54 is described below with reference to FIG. 7. Item (a) of FIG. 7 shows an arbitrary frame Fm of image data. The frame Fm is composed of pixels in an effective image period. The number of the pixels is, for example, 640 horizontal pixels and 480 vertical pixels in the VGA standard. For reasons of simplification, the number of the pixels in the frame Fm is greatly decreased so as to schematically show the frame Fm.

The image data generated by the imaging unit 3 having the Bayer array is data in which pixel data for R, G, and B are mixed in the frame Fm. The demosaicing unit 54 computes pixel data for R for pixel positions where no pixel data for R is present by use of the surrounding pixel data for R, so as to generate interpolated pixel data Ri for R. The demosaicing unit 54 generates R frame FmR in which all pixels in one frame shown in item (b) of FIG. 7 are composed of the pixel data for R.

The demosaicing unit 54 computes pixel data for G for pixel positions where no pixel data for G is present by use of the surrounding pixel data for G, so as to generate interpolated pixel data Gi for G. The demosaicing unit 54 generates G frame FmG in which all pixels in one frame shown in item (c) of FIG. 7 are composed of the pixel data for G.

The demosaicing unit 54 computes pixel data for B for pixel positions where no pixel data for B is present by use of the surrounding pixel data for B, so as to generate interpolated pixel data Bi for B. The demosaicing unit 54 generates B frame FmB in which all pixels in one frame shown in item (d) of FIG. 7 are composed of the pixel data for B.

The demosaicing unit 54 is only required to use at least the pixel data for R when interpolating the pixel data for R, use at least the pixel data for G when interpolating the pixel data for G, and use at least the pixel data for B when interpolating the pixel data for B. Alternatively, the demosaicing unit 54 may interpolate the pixel data for each of R, G, and B to be generated by use of the pixel data of the different colors in order to improve the accuracy of the interpolation.

Since the imaging unit 3 further includes pixels outside the effective image period, pixel data for each of R, G, and B can be interpolated with regard to the pixels located along the edges of top and bottom, left and right.

The R frame FmR, the G frame FmG and the B frame FmB generated by the demosaicing unit 54 are output as the data for the three primary colors R, G, and B. Although the pixel data for each of R, G, and B was described per frame in FIG. 7 for ease of explanation, the pixel data for each of R, G, and B is actually output sequentially per pixel.

<Intermediate Mode: First Intermediate Mode>

In the intermediate mode (first intermediate mode and second intermediate mode described below), the controller 7 directs the drive unit 8 to insert the dummy glass 22 between the optical lens 1 and the imaging unit 3. The projection controller 71 turns on the infrared projector 9 to project infrared light. The mode switching unit 72 connects the switches 51 and 53 to the respective terminals Ta.

Figure 8:
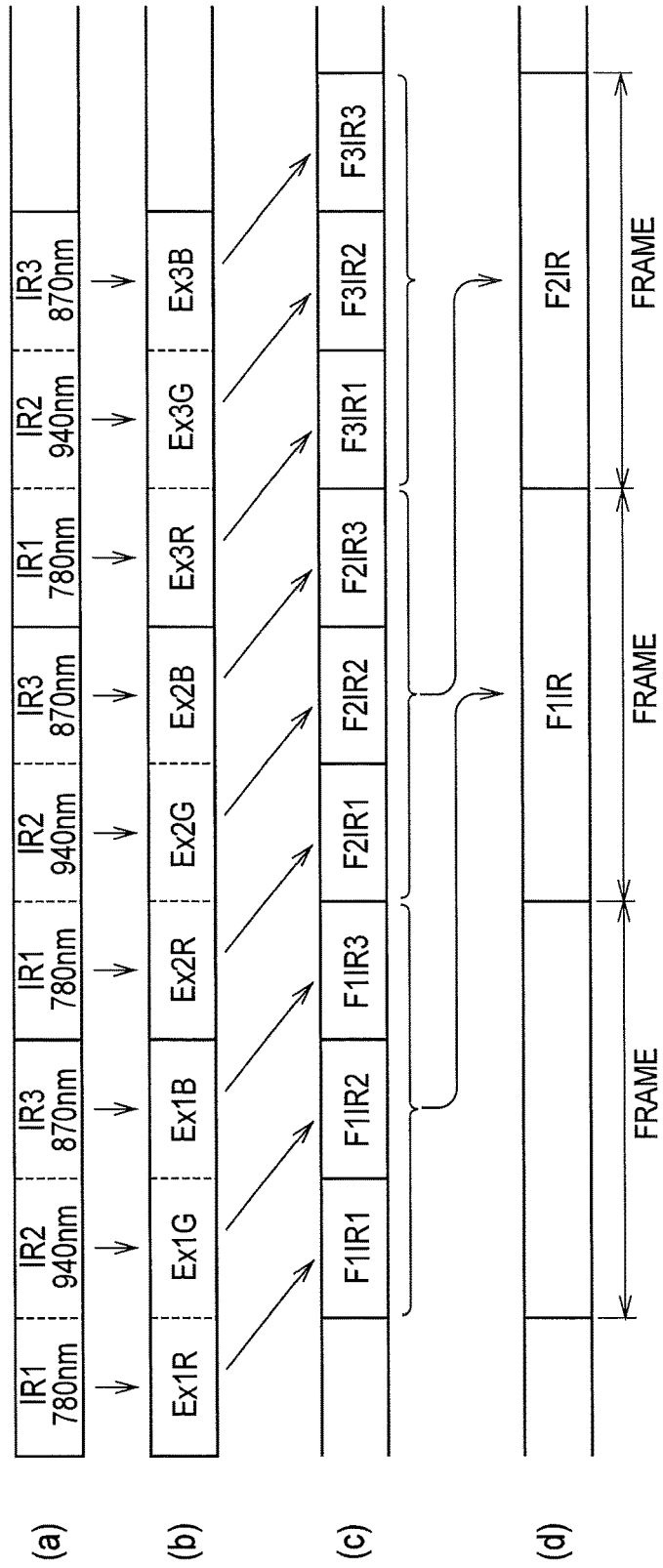
FIG. 8 is a view showing a relationship between exposures and frames of image signals when the imaging device according to the embodiment is operating in an intermediate mode and in a night-vision mode.

Item (a) of FIG. 8 shows a state where infrared light is projected from the infrared projector 9. The controller 7 divides one frame period of the normal mode into three so as to control the projecting portions 91, 92, and 93 to sequentially project infrared light in this order, for example.

In the example of item (a) of FIG. 8, the infrared light with the wavelength IR1 (780 nm) is radiated on the object in the first ⅓ period of the one frame. The infrared light with the wavelength IR2 (940 nm) is radiated on the object in the second ⅓ period of the one frame. The infrared light with the wavelength IR3 (870 nm) is radiated on the object in the last ⅓ period of the one frame. The order of radiation of the infrared light with the respective wavelengths IR1, IR2, and IR3 is optional.

As shown in item (b) of FIG. 8, exposure Ex1R which has a strong correlation with R light is executed by the imaging unit 3 at the point where the infrared light with the wavelength IR1 is being projected. Exposure Ex1G which has a strong correlation with G light is executed by the imaging unit 3 at the point where the infrared light with the wavelength IR2 is being projected. Exposure Ex1B which has a strong correlation with B light is executed by the imaging unit 3 at the point where the infrared light with the wavelength IR3 is being projected.

Note that, since an image is captured in the intermediate mode in a state where visible light is slightly present, visible light and infrared light projected from the infrared projector 9 coexist. Therefore, in the intermediate mode, exposures Ex1R, Ex1G, Ex1B, Ex2R, Ex2G, Ex2B, etc., are each obtained in a manner such that exposure of visible light and exposure of infrared light are combined together.

As shown in item (c) of FIG. 8, frame F1IR1 corresponding to the exposure Ex1R, frame F1IR2 corresponding to the exposure Ex1G, and frame F1IR3 corresponding to the exposure Ex1B are obtained based on the exposures Ex1R, Ex1G, and Ex1B after a predetermined period of time.

Further, frame F2IR1 corresponding to the exposure Ex2R, frame F2IR2 corresponding to the exposure Ex2G, and frame F2IR3 corresponding to the exposure Ex2B are obtained based on the exposures Ex2R, Ex2G, and Ex2B after a predetermined period of time. The same operations are repeated after the exposures Ex3R, Ex3G, and Ex3B.

The frame frequency of the imaging signals in item (c) of FIG. 8 is 90 frames per second. In the intermediate mode, one frame of the image signals in the normal mode is subjected to time division so as to project the infrared light with the respective wavelengths IR1 to IR3. Thus, in order to output the image signals in the same format as the normal mode, the frame frequency of the imaging signals in item (c) of FIG. 8 is three times as many as that in the normal mode.

As described below, based on the imaging signals of the three frames in item (c) of FIG. 8, one frame of image signals is generated, having a frame frequency of 30 frames per second, as shown in item (d) of FIG. 8. For example, frame F1IR is generated based on the frames F1IR1, F1IR2, and F1IR3. Frame F2IR is generated based on the frames F2IR1, F2IR2, and F2IR3.

The operation of generating the image signals of each frame in item (d) of FIG. 8 in the intermediate mode, based on the imaging signals of the three frames in item (c) of FIG. 8, is described in detail below.

The image data for the respective frames, corresponding to the imaging signals shown in item (c) of FIG. 8 output from the A/D converter 4, is input into the pre-signal processing unit 52 via the switch 51.

Figure 9:
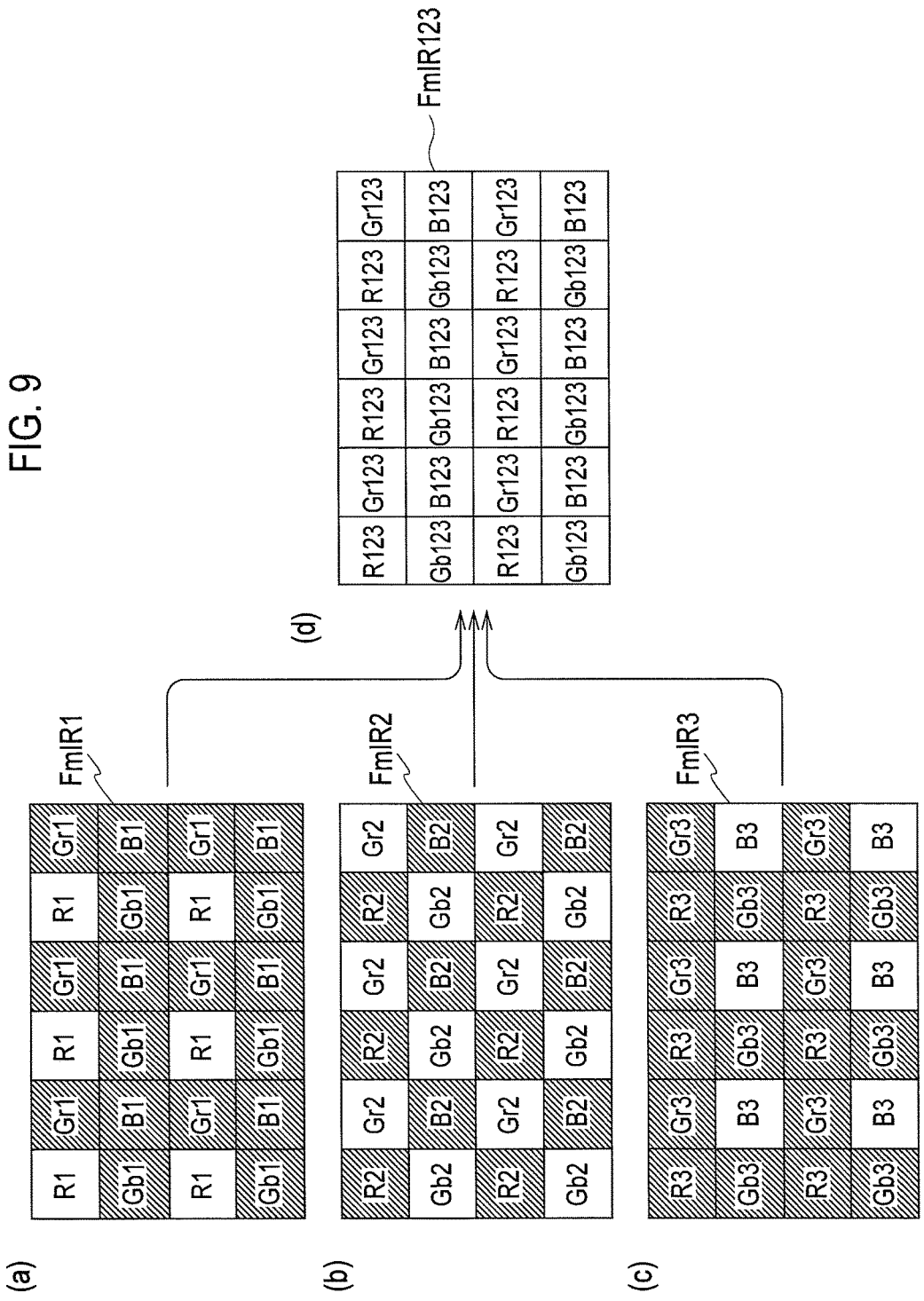
FIG. 9 is a view for describing pre-signal processing when the imaging device according to the embodiment is operating in a first intermediate mode.

Pre-signal processing in the pre-signal processing unit 52 is described below with reference to FIG. 9. Item (a) of FIG. 9 shows an arbitrary frame FmIR1 of image data generated at the point where the infrared light with the wavelength IR1 is being projected. The pixel data for each of R, B, Gr, and Gb in the frame FmIR1 is indicated with an index "1" indicating that all data is generated in the state where the infrared light with the wavelength IR1 is projected.

Item (b) of FIG. 9 shows an arbitrary frame FmIR2 of image data generated at the point where the infrared light with the wavelength IR2 is being projected. The pixel data for each of R, B, Gr, and Gb in the frame FmIR2 is indicated with an index "2" indicating that all data is generated in the state where the infrared light with the wavelength IR2 is projected.

Item (c) of FIG. 9 shows an arbitrary frame FmIR3 of image data generated at the point where the infrared light with the wavelength IR3 is being projected. The pixel data for each of R, B, Gr, and Gb in the frame FmIR3 is indicated with an index "3" indicating that all data is generated in the state where the infrared light with the wavelength IR3 is projected.

Since the frame FmIR1 shown in item (a) of FIG. 9 includes the image data generated in the state where the infrared light with the wavelength IR1 having a strong correlation with R light is projected, the pixel data for R is pixel data corresponding to the projected infrared light, and the pixel data for B and G are pixel data not corresponding to the projected infrared light. The hatching added to the pixel data for each of B, Gr, and Gb represents that the pixel data does not correspond to the projected infrared light.

Since the frame FmIR2 shown in item (b) of FIG. 9 includes the image data generated in the state where the infrared light with the wavelength IR2 having a strong correlation with G light is projected, the pixel data for G is pixel data corresponding to the projected infrared light, and the pixel data for R and B are pixel data not corresponding to the projected infrared light. The hatching added to the pixel data for each of R and B represents that the pixel data does not correspond to the projected infrared light.

Since the frame FmIR3 shown in item (c) of FIG. 9 includes the image data generated in the state where the infrared light with the wavelength IR3 having a strong correlation with B light is projected, the pixel data for B is pixel data corresponding to the projected infrared light, and the pixel data for R and G are pixel data not corresponding to the projected infrared light. The hatching added to the pixel data for each of R, Gr, and Gb represents that the pixel data does not correspond to the projected infrared light.

The same-position pixel adding unit 522 in the pre-signal processing unit 52 individually adds the pixel data for each of R, Gr, Gb, and B located at the same pixel positions according to the following formulae (1) to (3) so as to generate added pixel data R123, Gr123, Gb123, and B123. In the intermediate mode, the surrounding pixel adding unit 521 in the pre-signal processing unit 52 is inactive.

$$R123 = ka \times R1 + kb \times R2 + kc \times R3 \quad (1)$$

$$G123 = kd \times G1 + ke \times G2 + kf \times G3 \quad (2)$$

$$B123 = kg \times B1 + kh \times B2 + ki \times B3 \quad (3)$$

In the formulae (1) to (3), R1, G1, and B1 are pixel data for R, G, and B in the frame FmIR1, R2, G2, and B2 are pixel data for R, G, and B in the frame FmIR2, and R3, G3, and B3 are pixel data for R, G, and B in the frame FmIR3. In addition, ka to ki are predetermined coefficients. The data G123 in the formula (2) is either Gr123 or Gb123.

The same-position pixel adding unit 522 adds the hatched pixel data for each of R, Gr, Gb, and B to the pixel data for each of R, Gr, Gb, and B located at the same pixel positions not hatched.

In particular, the same-position pixel adding unit 522 adds, to the pixel data for R located in the frame FmIR1, the pixel data for R located at the same pixel positions in each of the frames FmIR2 and FmIR3, so as to generate the added pixel data R123 according to the formula (1). That is, the same-position pixel adding unit 522 only uses the pixel data in the region corresponding to the red color filter in the light receiving elements and generates the added pixel data R123 for red.

The same-position pixel adding unit 522 adds, to the pixel data for Gr, Gb located in the frame FmIR2, the pixel data for Gr, Gb located at the same pixel positions in each of the frames FmIR1 and FmIR3, so as to generate the added pixel data G123 according to the formula (2). That is, the same-position pixel adding unit 522 only uses the pixel data in the region corresponding to the green color filter in the light receiving elements and generates the added pixel data G123 for green.

The same-position pixel adding unit 522 adds, to the pixel data for B located in the frame FmIR3, the pixel data for B located at the same pixel positions in each of the frames FmIR1 and FmIR2, so as to generate the added pixel data B123 according to the formula (3). That is, the same-position pixel adding unit 522 only uses the pixel data in the region corresponding to the blue color filter in the light receiving elements and generates the added pixel data B123 for blue.

The synthesizing unit 523 in the pre-signal processing unit 52 generates frame FmIR123 of synthesized image signals shown in item (d) of FIG. 9 based on the respective added pixel data R123, Gr123, Gb123, and B123 generated at the respective pixel positions.

More particularly, the synthesizing unit 523 selects the added pixel data R123 in the frame FmIR1, the added pixel data Gr123 and Gb123 in the frame FmIR2, and the added pixel data B123 in FmIR3, and synthesizes the respective added pixel data. The synthesizing unit 523 thus generates the frame FmIR123 of the synthesized image signals.

As described above, the synthesizing unit 523 generates the frame FmIR123 in which the respective added pixel data R123, Gr123, Gb123, and B123 are arranged so as to have the same array as the filter elements in the color filter 32.

In the first intermediate mode, the image data in the frame FmIR123 are generated in such a manner as to use the pixel data not hatched and the pixel data hatched.

The reason the same-position pixel adding unit 522 adds the respective pixel data located at the same pixel positions is that, since an image is captured in the intermediate mode in the state where visible light is present, although the amount thereof is small, the hatched pixel data contains the components of the respective colors based on the exposure by the visible light. Therefore, the respective pixel data located at the same pixel positions are added to each other so that the sensitivity to the respective colors can be improved.

When the amount of visible light is relatively large in the state where visible light and infrared light coexist, the exposure by the visible light is predominant. In such a case, the image data in the frame FmIR123 mainly contains the components based on the image signals exposed by the visible light. When the amount of infrared light is relatively large in the state where infrared light and visible light coexist, the exposure by the infrared light is predominant. In such a case, the image data in the frame FmIR123 mainly contains the components based on the image signals exposed by the infrared light.

When the amount of visible light is relatively small, the coefficients ka, kb, and kc in the formula (1) preferably fulfill the relationship of ka>kb, kc, the coefficients kd, ke, and kf in the formula (2) preferably fulfill the relationship of kf>kd, ke, and the coefficients kg, kh, and ki in the formula (3) preferably fulfill the relationship of kh>kg, ki. This is because the wavelength IR1 has a strong correlation with the R light, the wavelength IR2 has a strong correlation with the G light, and the wavelength IR3 has a strong correlation with the B light.

Accordingly, the pixel data for R can be the main data in the frame FmIR1, the pixel data for G can be the main data in the frame FmIR2, and the pixel data for B can be the main data in the frame FmIR3.

The image data in the frame FmIR123 output from the pre-signal processing unit 52 is input into the demosaicing unit 54 via the switch 53. The demosaicing unit 54 subjects the input image data in the frame FmIR123 to demosaicing in the same manner as the normal mode. The image processing unit 5 subjects the image data to other types of image processing in addition to the demosaicing, and outputs the data for the three primary colors R, G, and B.

Figure 10:
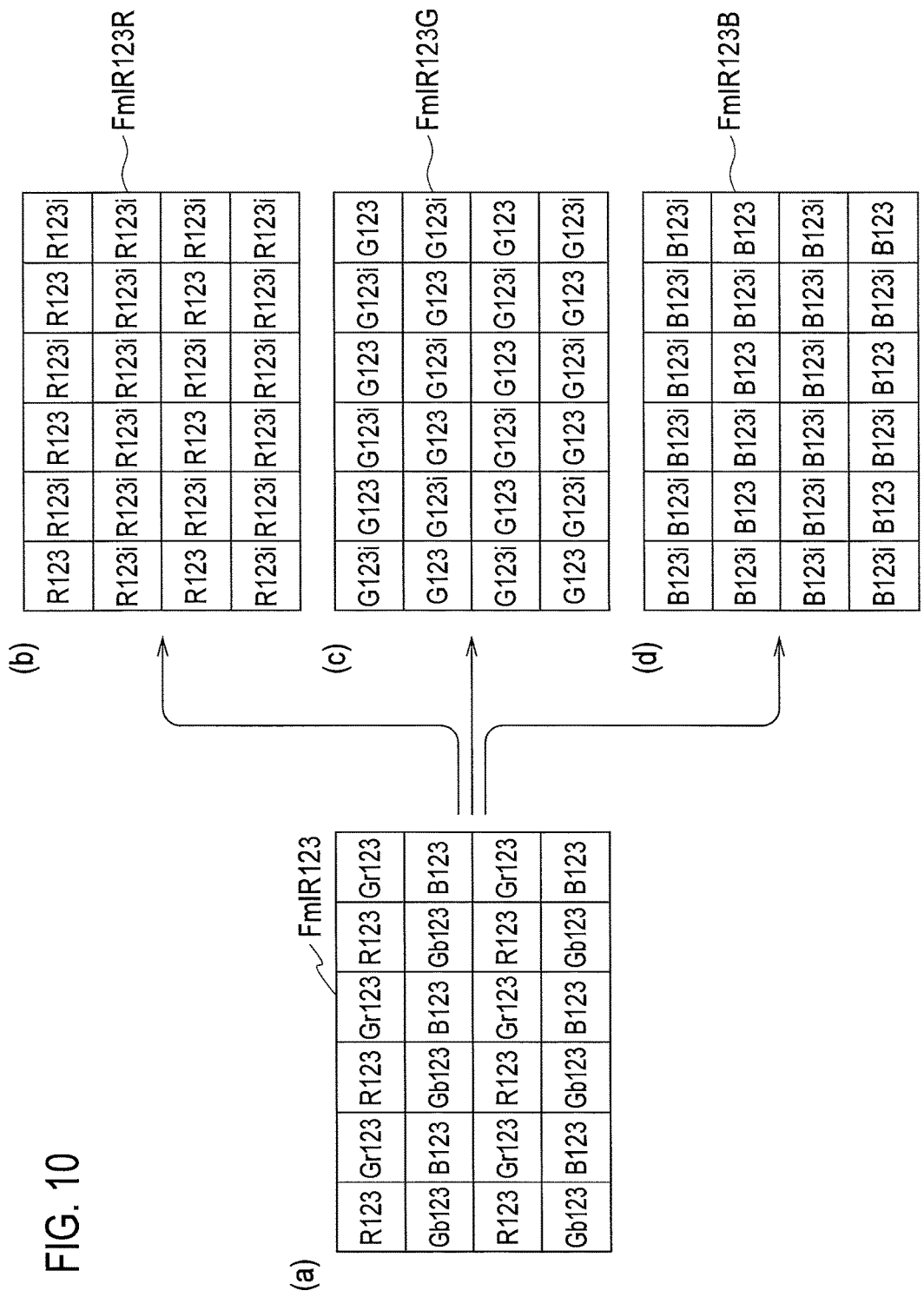
FIG. 10 is a view for describing demosaicing when the imaging device according to the embodiment is operating in the first intermediate mode.

The demosaicing in the demosaicing unit 54 is described below with reference to FIG. 10. Item (a) of FIG. 10 shows the frame FmIR123. The demosaicing unit 54 computes pixel data for R for pixel positions where no pixel data for R is present by use of the surrounding pixel data for R, so as to generate interpolated pixel data R123$i$ for R. The demosaicing unit 54 generates R frame FmIR123R in which all pixels in one frame shown in item (b) of FIG. 10 are composed of the pixel data for R.

The demosaicing unit 54 computes pixel data for G for pixel positions where no pixel data for G is present by use of the surrounding pixel data for G, so as to generate interpolated pixel data G123$i$ for G. The demosaicing unit 54 generates G frame FmIR123G in which all pixels in one frame shown in item (c) of FIG. 10 are composed of the pixel data for G.

The demosaicing unit 54 computes pixel data for B for pixel positions where no pixel data for B is present by use of the surrounding pixel data for B, so as to generate interpolated pixel data B123$i$ for B. The demosaicing unit 54 generates B frame FmIR123B in which all pixels in one frame shown in item (d) of FIG. 10 are composed of the pixel data for B.

As is apparent from the operation of the demosaicing unit 54 in the normal mode shown in FIG. 7 and the operation of the demosaicing unit 54 in the intermediate mode shown in FIG. 10, the both operations are substantially the same. Thus, the operation of the demosaicing unit 54 does not differ between the normal mode and the intermediate mode.

The pre-signal processing unit 52 is only required to be activated in the intermediate mode except for the surrounding pixel adding unit 521, while the pre-signal processing unit 52 is inactivated in the normal mode. The normal mode and the intermediate mode may share the signal processing unit such as the demosaicing unit 54 in the image processing unit 5.

<Intermediate Mode: Second Intermediate Mode>

Figure 11:
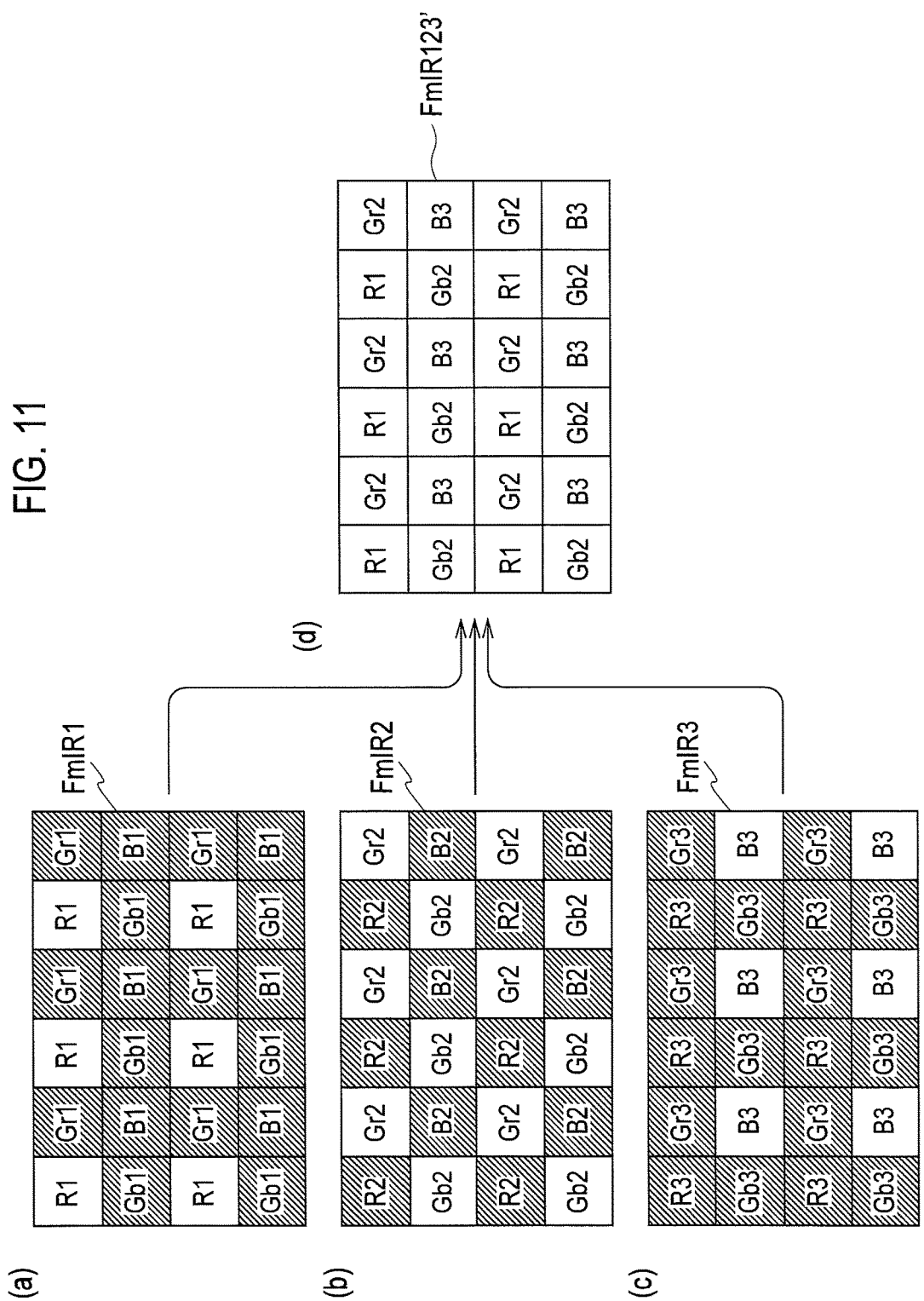
FIG. 11 is a view for describing pre-signal processing when the imaging device according to the embodiment is operating in a second intermediate mode.
Figure 12:
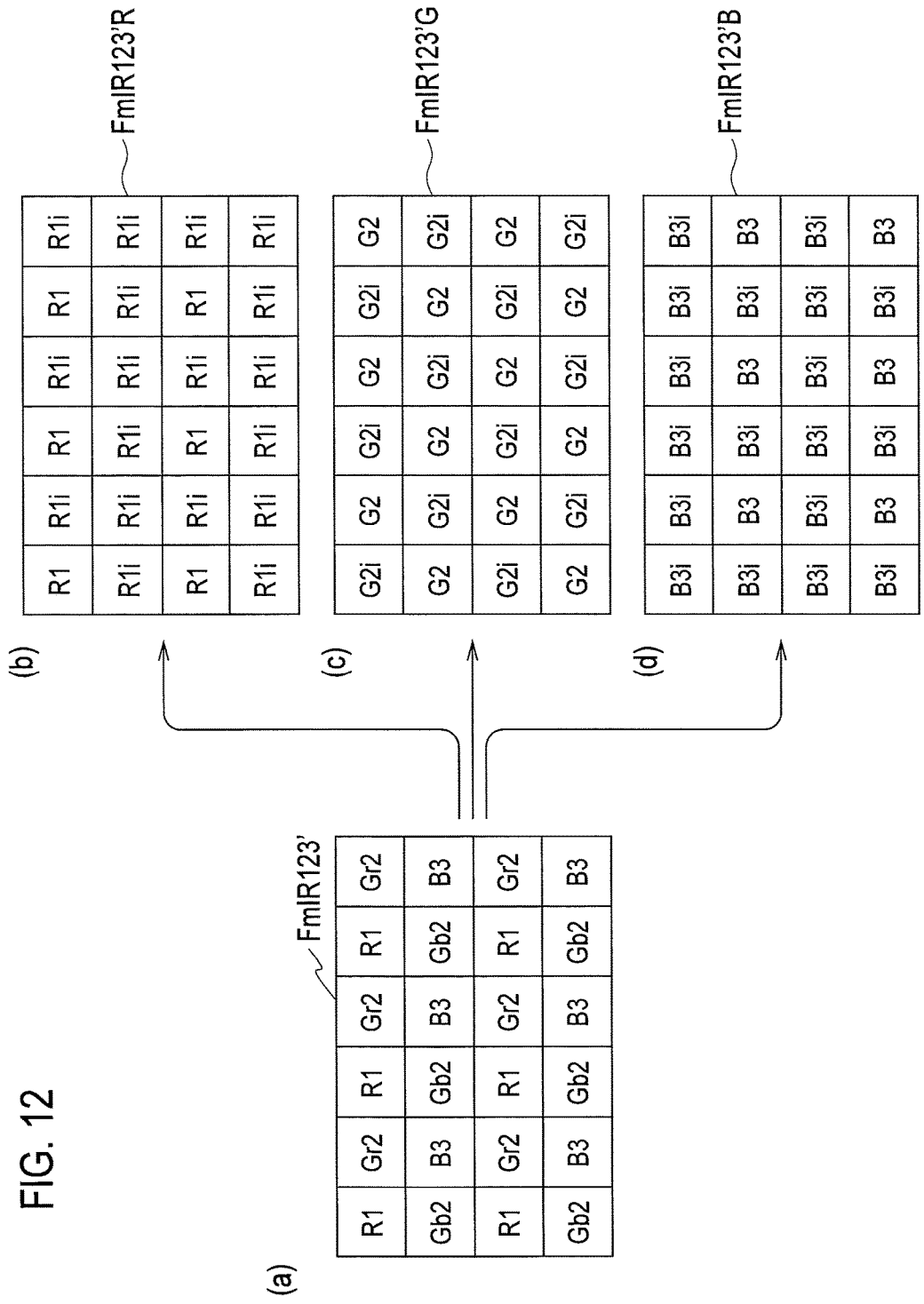
FIG. 12 is a view for describing demosaicing when the imaging device according to the embodiment is operating in the second intermediate mode.

Operations in the second intermediate mode are described below with reference to FIG. 11 and FIG. 12. Note that the same operations as those in the first intermediate mode are not repeated in the second intermediate mode. The frame FmIR1, the frame FmIR2, and the frame FmIR3 shown in items (a) to (c) in FIG. 11 are the same as the frame FmIR1, the frame FmIR2, and the frame FmIR3 shown in items (a) to (c) in FIG. 9.

The synthesizing unit 523 selects pixel data R1 for R in the frame FmIR1, pixel data Gr2 and Gb2 for G in the frame FmIR2, and pixel data B3 for B in FmIR3, and synthesizes the respective pixel data. The synthesizing unit 523 thus generates frame FmIR123' of the synthesized image signals shown in item (d) of FIG. 11.

That is, the frame FmIR123' is image data in which the pixel data for R, Gr, Gb, and B not hatched in each of the frames FmIR1, FmIR2, and FmIR3 are collected in one frame.

Thus, the frame FmIR123' contains the pixel data for red only using the pixel data in the region corresponding to the red color filter in the state where the infrared light with the wavelength IR1 is projected, the pixel data for green only using the pixel data in the region corresponding to the green color filter in the state where the infrared light with the wavelength IR2 is projected, and the pixel data for blue only using the pixel data in the region corresponding to the blue color filter in the state where the infrared light with the wavelength IR3 is projected.

As described above, the synthesizing unit 523 generates the frame FmIR123' in which the respective pixel data R1, Gr2, Gb2, and B3 are arranged so as to have the same array as the filter elements in the color filter 32.

In the second intermediate mode, the same-position pixel adding unit 522 defines the coefficient ka in the formula (1) as 1 and the other coefficients kb and kc as 0, defines the coefficient ke in the formula (2) as 1 and the other coefficients kd and kf as 0, and defines the coefficient ki in the formula (3) as 1 and the other coefficients kg and kh as 0.

Therefore, the value of the pixel data for R in the frame FmIR1, the values of the pixel data for Gr and Gb in the frame FmIR2, and the value of the pixel data for B in the frame FmIR3 each remain as is.

Accordingly, the synthesizing unit 523 can generate the frame FmIR123' by selecting the pixel data for R in the frame FmIR1, the pixel data for Gr and Gb in the frame FmIR2, and the pixel data for B in the frame FmIR3, in the same manner as the operations in the first intermediate mode.

In the second intermediate mode, the pre-signal processing unit 52 only uses the pixel data (the pixel data not hatched) generated in the state where the infrared light for generating the pixel data with the same color is projected so as to generate the frame FmIR123'.

According to the second intermediate mode, although the sensitivity or color reproduction performance decreases compared with the first intermediate mode, the calculation processing can be simplified or the frame memory can be reduced.

The demosaicing in the demosaicing unit 54 is described below with reference to FIG. 12. Item (a) of FIG. 12 shows the frame FmIR123'. The demosaicing unit 54 computes pixel data for R for pixel positions where no pixel data for R is present by use of the surrounding pixel data for R, so as to generate interpolated pixel data R1$i$ for R. The demosaicing unit 54 generates R frame FmIR123'R in which all pixels in one frame shown in item (b) of FIG. 12 are composed of the pixel data for R.

The demosaicing unit 54 computes pixel data for G for pixel positions where no pixel data for G is present by use of the surrounding pixel data for G, so as to generate interpolated pixel data G2$i$ for G. The demosaicing unit 54 generates G frame FmIR123'G in which all pixels in one frame shown in item (c) of FIG. 12 are composed of the pixel data for G.

The demosaicing unit 54 computes pixel data for B for pixel positions where no pixel data for B is present by use of the surrounding pixel data for B, so as to generate interpolated pixel data B3$i$ for B. The demosaicing unit 54 generates B frame FmIR123'B in which all pixels in one frame shown in item (d) of FIG. 12 are composed of the pixel data for B.

Accordingly, in the intermediate mode, the pixel data for red is generated from the pixel data obtained from the region corresponding to the red color filter in the light receiving elements, the pixel data for green is generated from the pixel data obtained from the region corresponding to the green color filter in the light receiving elements, and the pixel data for blue is generated from the pixel data obtained from the region corresponding to the blue color filter in the light receiving elements.

<Night-Vision Mode: First Night-Vision Mode>

In the night-vision mode (first night-vision mode and second night-vision mode described below), the controller 7 directs the drive unit 8 to insert the dummy glass 22 between the optical lens 1 and the imaging unit 3, as in the case of the intermediate mode. The projection controller 71 turns on the infrared projector 9 to project infrared light. The mode switching unit 72 connects the switches 51 and 53 to the respective terminals Ta.

The general operations in the night-vision mode are the same as those shown in FIG. 8. However, since an image is captured in the night-vision mode in a state where almost no visible light is present, the exposures Ex1R, Ex1G, Ex1B, Ex2R, Ex2G, Ex2B, etc., shown in item (b) of FIG. 8 are assumed to be exposure only by infrared light.

Under the condition that there is almost no visible light but only infrared light, the characteristics of the respective filter elements in the color filter 32 do not differ from each other. Thus, the imaging unit 3 can be considered as a single-color imaging device.

Therefore, in the night-vision mode, the surrounding pixel adding unit 521 in the pre-signal processing unit 52 adds surrounding pixel data to all pixel data in order to improve the sensitivity of infrared light.

More particularly, when the R pixel is the target pixel as shown in item (a) of FIG. 13, the surrounding pixel adding unit 521 adds, to the pixel data for R as the target pixel, the pixel data of the surrounding eight pixels of G (Gr, Gb) and B.

While the pixel data for red is generated from the pixel data obtained from the region corresponding to the red color filter in the light receiving elements in the intermediate mode, the pixel data for red is generated, in the night-vision mode, from the pixel data obtained from a wider region than the region in the intermediate mode. The respective examples shown in items (a) to (d) of FIG. 13 use the pixel data obtained from the region of the nine pixels including the target pixel.

When the Gr pixel is the target pixel as shown in item (b) of FIG. 13, the surrounding pixel adding unit 521 adds, to the pixel data for Gr as the target pixel, the pixel data of the surrounding eight pixels of R, Gb, and B. When the Gb pixel is the target pixel as shown in item (c) of FIG. 13, the surrounding pixel adding unit 521 adds, to the pixel data for Gb as the target pixel, the pixel data of the surrounding eight pixels of R, Gr, and B.

While the pixel data for green is generated from the pixel data obtained from the region corresponding to the green color filter in the light receiving elements in the intermediate mode, the pixel data for green is generated, in the night-vision mode, from the pixel data obtained from a wider region than the region in the intermediate mode.

When the B pixel is a target pixel as shown in item (d) of FIG. 13, the surrounding pixel adding unit 521 adds, to the pixel data for B as the target pixel, the pixel data of the surrounding eight pixels of R and G.

While the pixel data for blue is generated from the pixel data obtained from the region corresponding to the blue color filter in the light receiving elements in the intermediate mode, the pixel data for blue is generated, in the night-vision mode, from the pixel data obtained from a wider region than the region in the intermediate mode.

The surrounding pixel adding unit 521 may simply add the pixel data of the nine pixels together including the target pixel and the surrounding eight pixels, or may add, to the pixel data of the target pixel, the pixel data of the surrounding eight pixels after being subjected to particular weighting processing.

There is a known imaging element capable of collectively reading out a plurality of pixels as a single pixel, which is called binning. When the imaging element possessing the binning function is used as the imaging element 31, the adding processing may be performed not by the surrounding pixel adding unit 521 but by the imaging element with this binning function. The binning processing performed by the imaging element is substantially equivalent to the adding processing performed by the surrounding pixel adding unit 521.

Figure 14:
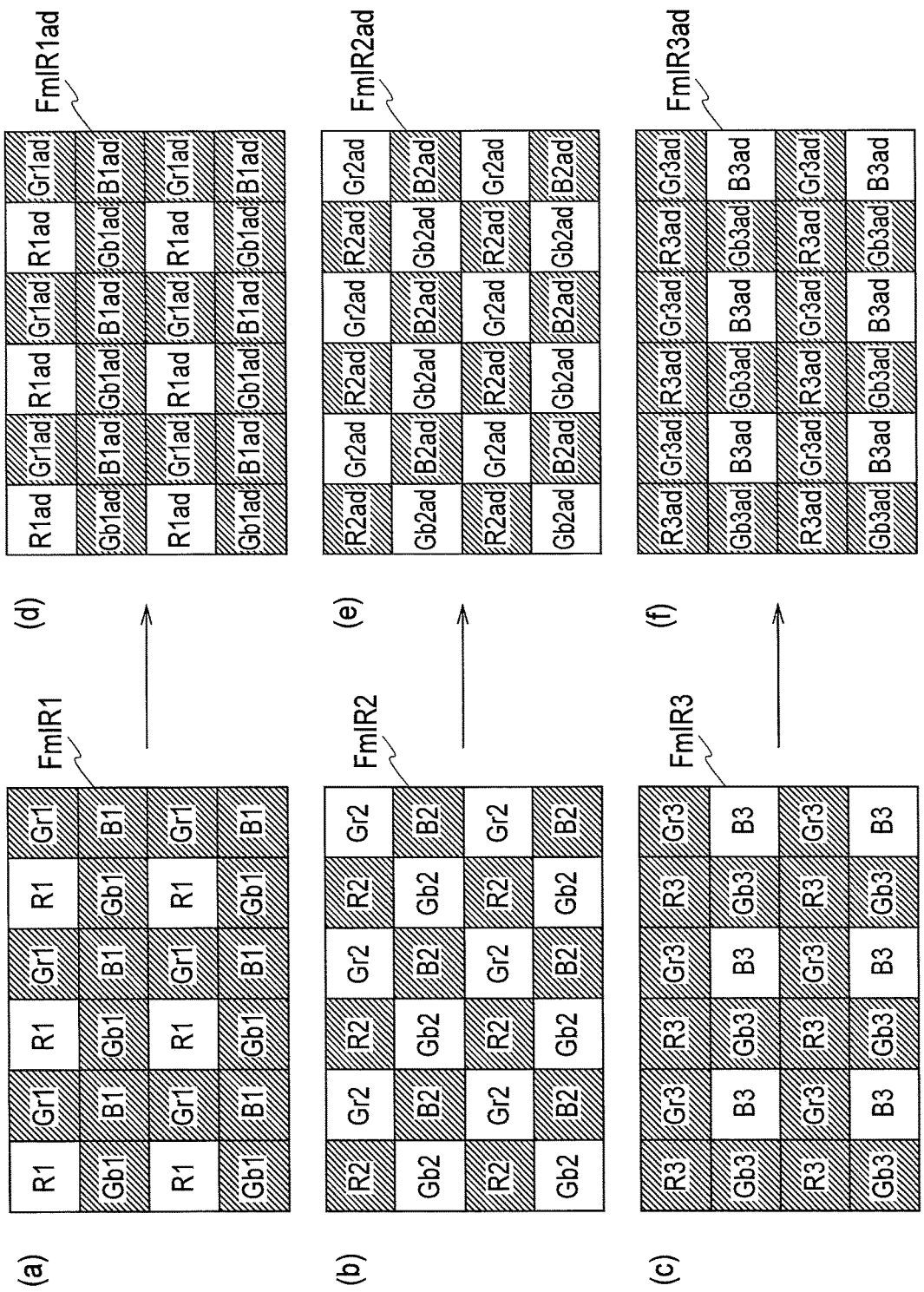
FIG. 14 is a view showing frames on which the processing of adding the surrounding pixels is performed.

The frames FmIR1, FmIR2, and FmIR3 shown in items (a) to (c) of FIG. 14 are the same as the frames FmIR1, FmIR2, and FmIR3 shown in items (a) to (c) of FIG. 9, respectively. In items (d) to (f) of FIG. 14, each of added pixel data R1$ad$, Gr1$ad$, Gb1$ad$, B1$ad$, R2$ad$, Gr2$ad$, Gb2$ad$, B2$ad$, R3$ad$, Gr3$ad$, Gb3$ad$, and B3$ad$ is obtained in a manner such that the pixel data of the surrounding eight pixels are added to the pixel data for each of R, Gr, Gb, and B.

The surrounding pixel adding unit 521 subjects the pixel data in each of the frames FmIR1, FmIR2, and FmIR3 to adding processing shown in FIG. 13, so as to generate frame FmIR1$ad$, frame FmIR2$ad$, and frame FmIR3$ad$ shown in items (d) to (f) of FIG. 14.

Figure 15:
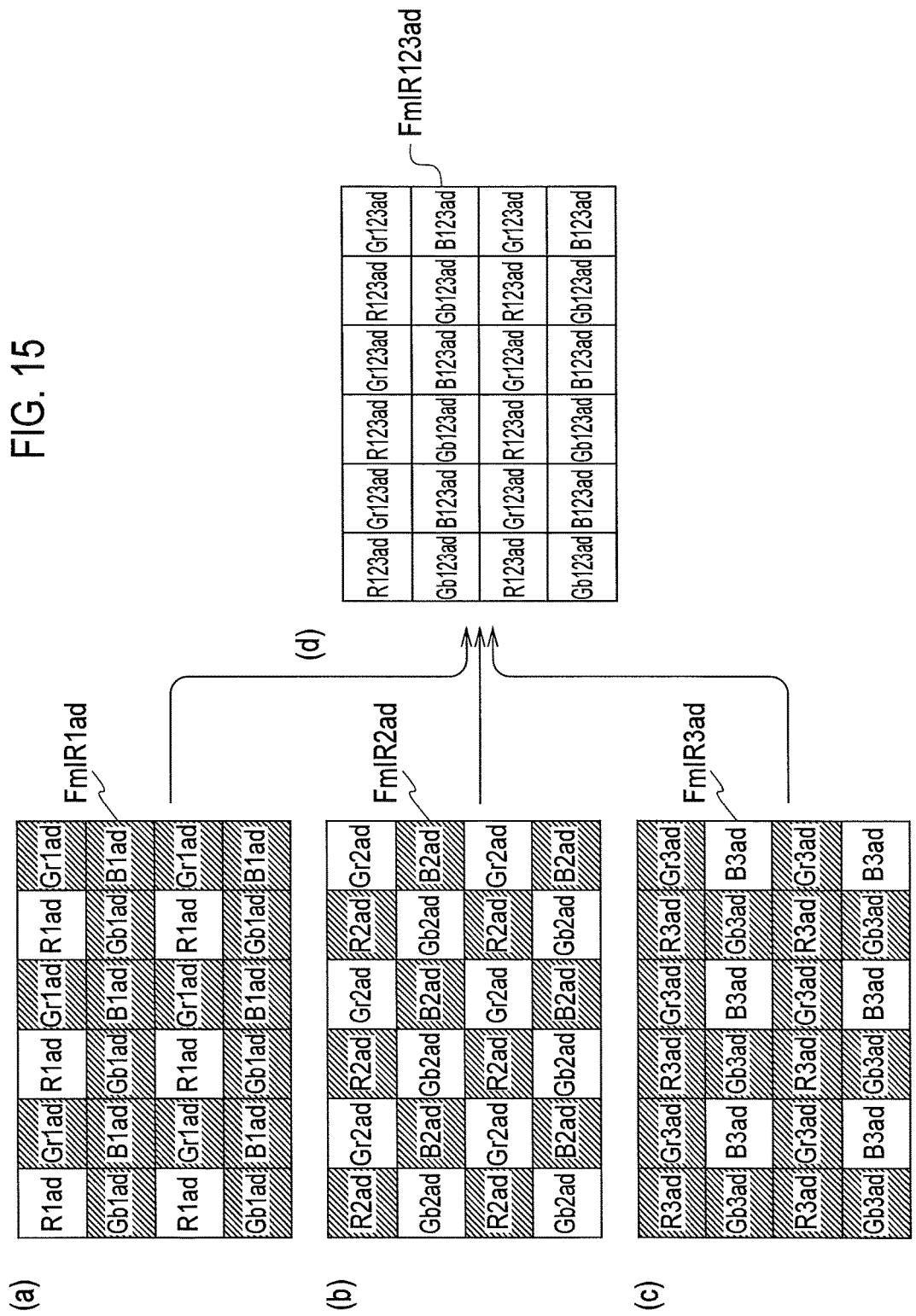
FIG. 15 is a view for describing pre-signal processing when the imaging device according to the embodiment is operating in a first night-vision mode.

The frames FmIR1$ad$, FmIR2$ad$, and FmIR3$ad$ shown in items (a) to (c) of FIG. 15 are the same as the frames FmIR1$ad$, FmIR2$ad$, and FmIR3$ad$ shown in items (d) to (f) of FIG. 14, respectively.

As in the case of the first intermediate mode, the same-position pixel adding unit 522 adds, to the pixel data R1$ad$ located in the frame FmIR1$ad$, the pixel data R2$ad$ and R3$ad$ located at the same pixel positions in the respective frames FmIR2$ad$ and FmIR3$ad$, so as to generate added pixel data R123$ad$ according to the formula (1).

The same-position pixel adding unit 522 adds, to the pixel data Gr2$ad$ and Gb2$ad$ located in the frame FmIR2$ad$, the pixel data Gr1$ad$, Gb1$ad$, Gr3$ad$, and Gb3$ad$ located at the same pixel positions in the respective frames FmIR1$ad$ and FmIR3$ad$, so as to generate added pixel data Gr123$ad$ and Gb123$ad$ according to the formula (2).

The same-position pixel adding unit 522 adds, to the pixel data B3$ad$ located in the frame FmIR3$ad$, the pixel data B1$ad$ and B2$ad$ located at the same pixel positions in the respective frames FmIR1$ad$ and FmIR2$ad$, so as to generate added pixel data B123$ad$ according to the formula (3).

As in the case of the first intermediate mode, the synthesizing unit 523 selects the added pixel data R123$ad$ in the frame FmIR1$ad$, the added pixel data Gr123$ad$ and Gb123$ad$ in the frame FmIR2$ad$, and the added pixel data B123$ad$ in FmIR3$ad$, and synthesizes the respective added pixel data. The synthesizing unit 523 thus generates frame FmIR123$ad$ of the synthesized image signals shown in item (d) of FIG. 15.

The synthesizing unit 523 generates the frame FmIR123$ad$ in which the respective added pixel data R123$ad$, Gr123$ad$, Gb123$ad$, and B123$ad$ are arranged so as to have the same array as the filter elements in the color filter 32.

Figure 16:
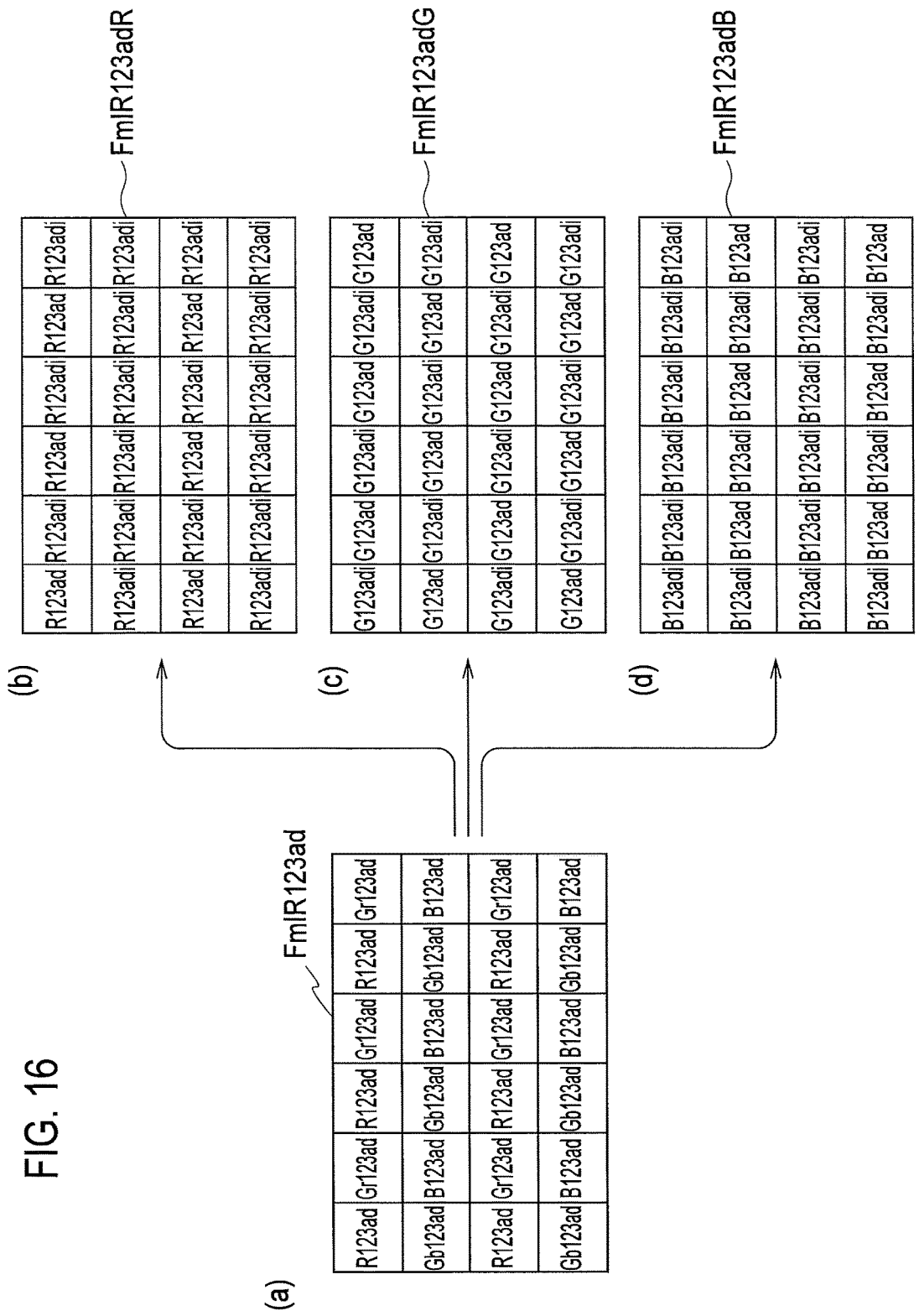
FIG. 16 is a view for describing demosaicing when the imaging device according to the embodiment is operating in the first night-vision mode.

Item (a) of FIG. 16 shows the frame FmIR123$ad$. The demosaicing unit 54 computes pixel data for R for pixel positions where no pixel data for R is present by use of the surrounding pixel data for R, so as to generate interpolated pixel data R123$adi$ for R. The demosaicing unit 54 generates R frame FmIR123$ad$R in which all pixels in one frame shown in item (b) of FIG. 16 are composed of the pixel data for R.

The demosaicing unit 54 computes pixel data for G for pixel positions where no pixel data for G is present by use of the surrounding pixel data for G, so as to generate interpolated pixel data G123$adi$ for G. The demosaicing unit 54 generates G frame FmIR123$ad$G in which all pixels in one frame shown in item (c) of FIG. 16 are composed of the pixel data for G.

The demosaicing unit 54 computes pixel data for B for pixel positions where no pixel data for B is present by use of the surrounding pixel data for B, so as to generate interpolated pixel data B123$adi$ for B. The demosaicing unit 54 generates B frame FmIR123$ad$B in which all pixels in one frame shown in item (d) of FIG. 16 are composed of the pixel data for B.

The first intermediate mode and the first night-vision mode differ from each other in that the surrounding pixel adding unit 521 is inactive in the first intermediate mode, and the surrounding pixel adding unit 521 is active in the first night-vision mode. The mode switching unit 72 is only required to activate the surrounding pixel adding unit 521 when in the night-vision mode.

The operation of the demosaicing unit 54 in the night-vision mode is substantially the same as that in the normal mode and in the intermediate mode. The normal mode, the intermediate mode, and the night-vision mode may share the signal processing unit such as the demosaicing unit 54 in the image processing unit 5.

<Night-Vision Mode: Second Night-Vision Mode>

Figure 17:
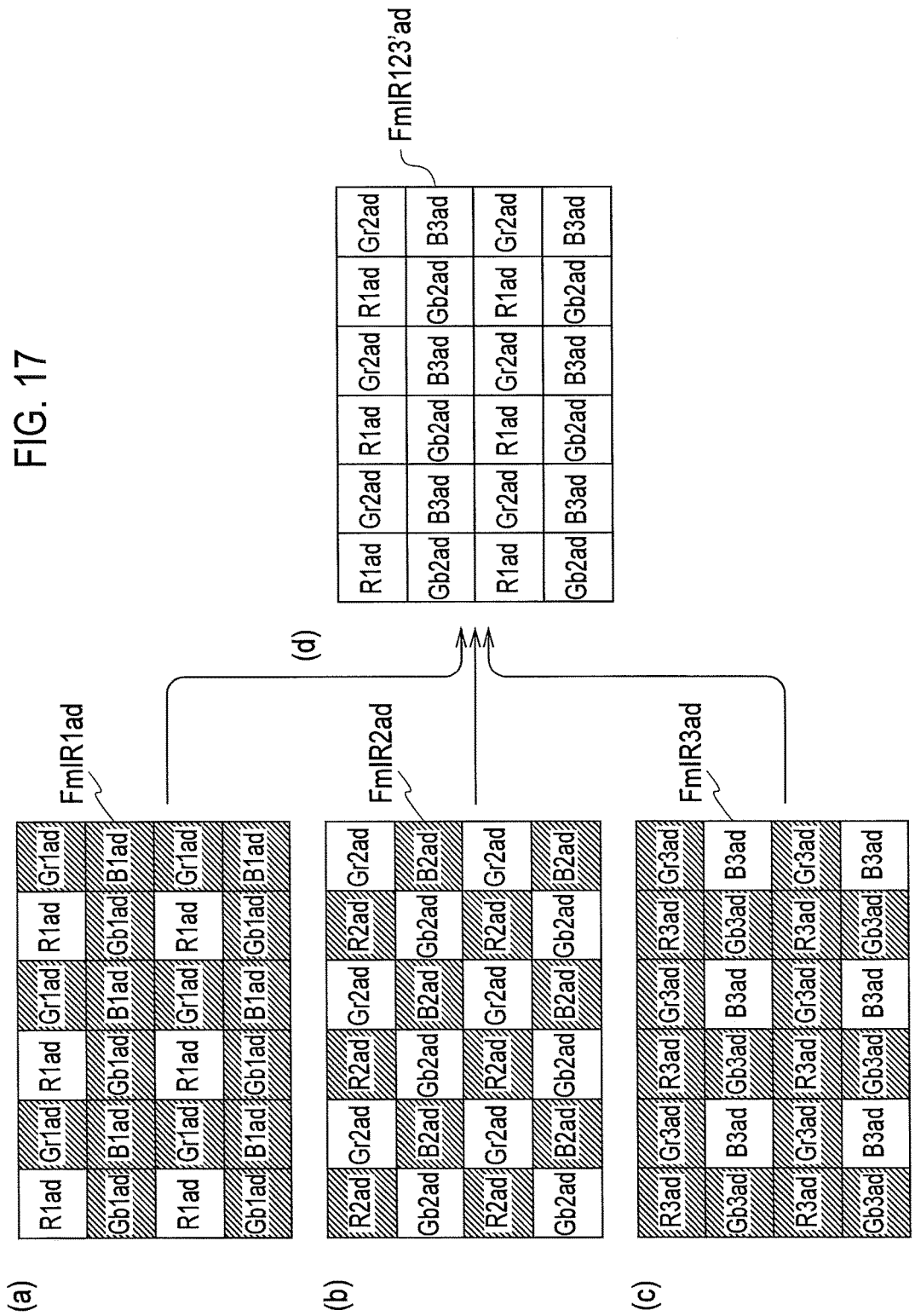
FIG. 17 is a view for describing pre-signal processing when the imaging device according to the embodiment is operating in a second night-vision mode.
Figure 18:
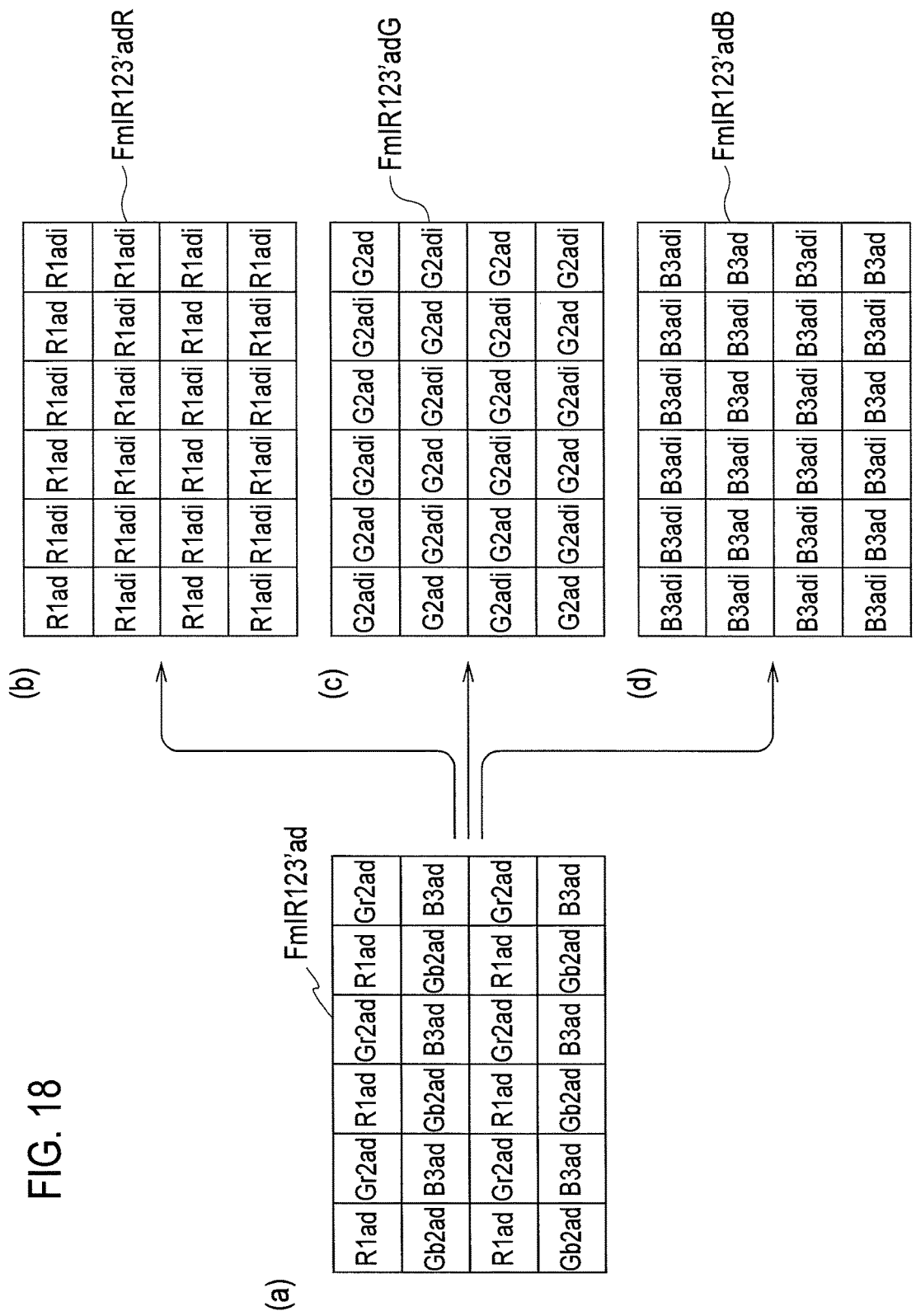
FIG. 18 is a view for describing demosaicing when the imaging device according to the embodiment is operating in the second night-vision mode.

Operations in the second night-vision mode are described below with reference to FIG. 17 and FIG. 18. Note that the same operations as those in the first night-vision mode are not described in the second night-vision mode. The frames FmIR1*ad*, FmIR2*ad*, and FmIR3*ad* shown in items (a) to (c) in FIG. 17 are the same as the frames FmIR1*ad*, FmIR2*ad*, and FmIR3*ad* shown in items (a) to (c) in FIG. 15.

The synthesizing unit 523 selects pixel data R1*ad* for R in the frame FmIR1*ad*, pixel data Gr2*ad* and Gb2*ad* for G in the frame FmIR2*ad*, and pixel data B3*ad* for B in FmIR3*ad* and synthesizes the respective pixel data. The synthesizing unit 523 thus generates frame FmIR123'*ad* of the synthesized image signals shown in item (d) of FIG. 17.

The synthesizing unit 523 generates the frame FmIR123'*ad* in which the respective pixel data R1*ad*, Gr2*ad*, Gb2*ad*, and B3*ad* are arranged so as to have the same array as the filter elements in the color filter 32.

As described with reference to FIG. 13, the pixel data R1*ad* for red in the frame FmIR123' ad is generated from the pixel data obtained from a wider region than the region used for generating the pixel data for red when in the intermediate mode.

The pixel data Gr2*ad* for green in the frame FmIR123' ad is generated from the pixel data obtained from a wider region than the region used for generating the pixel data for green when in the intermediate mode.

The pixel data B3*ad* for blue in the frame FmIR123' ad is generated from the pixel data obtained from a wider region than the region used for generating the pixel data for blue when in the intermediate mode.

As in the case of the second intermediate mode, the same-position pixel adding unit 522 in the second night-vision mode defines the coefficient ka in the formula (1) as 1 and the other coefficients kb and kc as 0, defines the coefficient ke in the formula (2) as 1 and the other coefficients kd and kf as 0, and defines the coefficient ki in the formula (3) as 1 and the other coefficients kg and kh as 0.

Therefore, the value of the pixel data R1*ad* in the frame FmIR1*ad*, the values of the pixel data Gr2*ad* and Gb2*ad* in the frame FmIR2*ad*, and the value of the pixel data B3*ad* in the frame FmIR3*ad* each remain as is.

Accordingly, the synthesizing unit 523 can generate the frame FmIR123' ad by selecting the pixel data R1*ad* in the frame FmIR1*ad*, the pixel data Gr2*ad* and Gb2*ad* in the frame FmIR2*ad*, and the pixel data B3*ad* in the frame FmIR3*ad*, in the same manner as the operations in the first night-vision mode.

The demosaicing in the demosaicing unit 54 is described below with reference to FIG. 18. Item (a) of FIG. 18 shows the frame FmIR123'*ad*. The demosaicing unit 54 computes pixel data for R for pixel positions where no pixel data for R is present by use of the surrounding pixel data R1*ad*, so as to generate interpolated pixel data R1*adi* for R. The demosaicing unit 54 generates R frame FmIR123'adR in which all pixels in one frame shown in item (b) of FIG. 18 are composed of the pixel data for R.

The demosaicing unit 54 computes pixel data for G for pixel positions where no pixel data for G is present by use of the surrounding pixel data Gr2*ad* and Gb2*ad*, so as to generate interpolated pixel data G2*adi* for G. The demosaicing unit 54 generates G frame FmIR123'adG in which all pixels in one frame shown in item (c) of FIG. 18 are composed of the pixel data for G.

The demosaicing unit 54 computes pixel data for B for pixel positions where no pixel data for B is present by use of the surrounding pixel data B3*ad*, so as to generate interpolated pixel data B3*adi* for B. The demosaicing unit 54 generates B frame FmIR123'adB in which all pixels in one frame shown in item (d) of FIG. 18 are composed of the pixel data for B.

The second intermediate mode and the second night-vision mode differ from each other in that the surrounding pixel adding unit 521 is inactive in the second intermediate mode, and the surrounding pixel adding unit 521 is active in the second night-vision mode.

While the pixel data for each color is generated from the pixel data obtained from the region corresponding to each color filter in the light receiving elements in the intermediate mode, the pixel data for each color is generated, in the night-vision mode, from the pixel data obtained from a wider region than the region used for generating the pixel data for each color in the intermediate mode, as the surrounding pixels are added in the night-vision mode.

<Example of Mode Switch>

An example of mode switching by the mode switching unit 72 is described below with reference to FIG. 19. Item (a) of FIG. 19 is an example schematically showing a state of change in environmental brightness with the passage of time from daytime to nighttime.

As shown in item (a) of FIG. 19, the brightness gradually decreases with the passage of time from daytime to nighttime, and results in almost total darkness after time t3. Item (a) of FIG. 19 shows the brightness representing a substantial amount of visible light, and indicates that almost no visible light is present after time t3.

The controller 7 can determine the environmental brightness based on a brightness level of image signals (image data) input from the image processing unit 5. As shown item (b) of FIG. 19, the mode switching unit 72 selects the normal mode when the brightness is predetermined threshold Th1 (first threshold) or greater, selects the intermediate mode when the brightness is less than the threshold Th1 and predetermined threshold Th2 (second threshold) or greater, and selects the night-vision mode when the brightness is less than the threshold Th2.

The imaging device according to the present embodiment automatically switches the modes in such a manner as to select the normal mode by time t1 at which the brightness reaches the threshold Th1, select the intermediate mode in the period from time t1 to time t2 at which the brightness reaches the threshold Th2, and select the night-vision mode after time t2. In item (b) of FIG. 19, the intermediate mode may be either the first intermediate mode or the second intermediate mode, and the night-vision mode may be either the first night-vision mode or the second night-vision mode.

Although the brightness immediately before time t3 at which almost no visible light remains is defined as the threshold Th2 in item (a) of FIG. 19, the brightness at time t3 may be defined as the threshold Th2.

As shown in item (c) of FIG. 19, the mode switching unit 72 may divide the intermediate mode into two periods: a first half period toward time t1 as the first intermediate mode in which the amount of visible light is relatively high; and a second half period toward time t2 as the second intermediate mode in which the amount of visible light is relatively low. In item (c) of FIG. 19, the night-vision mode may be either the first night-vision mode or the second night-vision mode.

In the imaging device according to the present embodiment, the projection controller 71 controls the ON/OFF state of the infrared projector 9, and the mode switching unit 72 switches the respective members in the image processing unit 5 between the active state and the inactive state, so as to implement the respective modes.

As shown in FIG. 20, the normal mode is a state where the infrared projector 9 is turned OFF, the surrounding pixel adding unit 521, the same-position pixel adding unit 522, and the synthesizing unit 523 are inactive, and the demosaicing unit 54 is active.

The first intermediate mode is implemented in a state where the infrared projector 9 is turned ON, the surrounding pixel adding unit 521 is inactive, and the same-position pixel adding unit 522, the synthesizing unit 523, and the demosaicing unit 54 are active. The second intermediate mode is implemented in a state where the infrared projector 9 is turned ON, the surrounding pixel adding unit 521 and the same-position pixel adding unit 522 are inactive, and the synthesizing unit 523 and the demosaicing unit 54 are active.

The same-position pixel adding unit 522 can be easily switched between the active state and the inactive state by appropriately setting the coefficients ka to ki in the formulae (1) to (3), as described above.

The first night-vision mode is implemented in a state where the infrared projector 9 is turned ON, and the surrounding pixel adding unit 521, the same-position pixel adding unit 522, the synthesizing unit 523, and the demosaicing unit 54 are all active. The second night-vision mode is implemented in a state where the infrared projector 9 is turned ON, the same-position pixel adding unit 522 is inactive, and the surrounding pixel adding unit 521, the synthesizing unit 523, and the demosaicing unit 54 are active.

The surrounding pixel adding unit 521 can be activated in the processing of adding the surrounding pixels by setting the coefficient to greater than 0 (for example, 1) by which the surrounding pixel data is multiplied in the calculation formula used for adding the surrounding pixel data to the pixel data of the target pixel.

The surrounding pixel adding unit 521 can be inactivated in the processing of adding the surrounding pixels by setting the coefficient to 0 by which the surrounding pixel data is multiplied in the calculation formula.

The surrounding pixel adding unit 521 thus can easily be switched between the active state and the inactive state by setting the coefficient as appropriate.

<First Modified Example of Imaging Device>

The method of detecting the environmental brightness by the controller 7 is not limited to the method based on the brightness level of the image signals.

Figure 21:
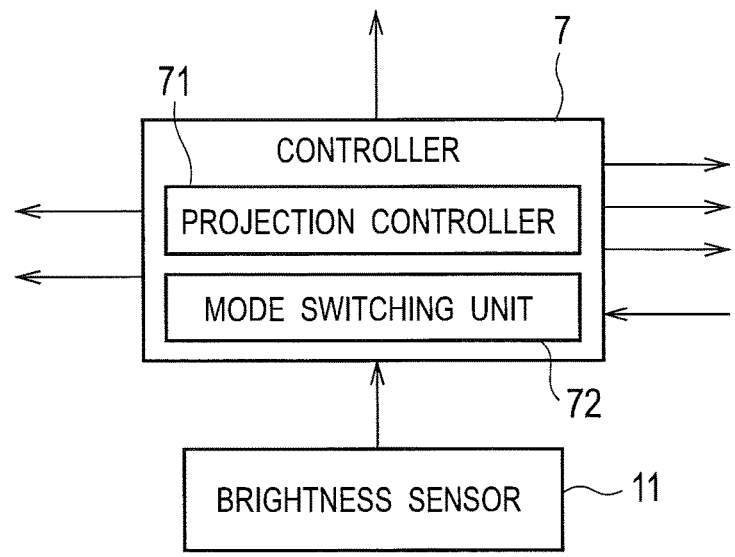
FIG. 21 is a partial block diagram showing a first modified example of the imaging device according to the embodiment.

As shown in FIG. 21, the environmental brightness may be detected by a brightness sensor 11. In FIG. 21, the environmental brightness may be determined based on both the brightness level of the image signals and the environmental brightness detected by the brightness sensor 11.

<Second Modified Example of Imaging Device>

The controller 7 may briefly estimate the environmental brightness based on the season (date) and the time (time zone) during a year, instead of the direct detection of the environmental brightness, so as to switch the modes by the mode switching unit 72.

Figure 22:
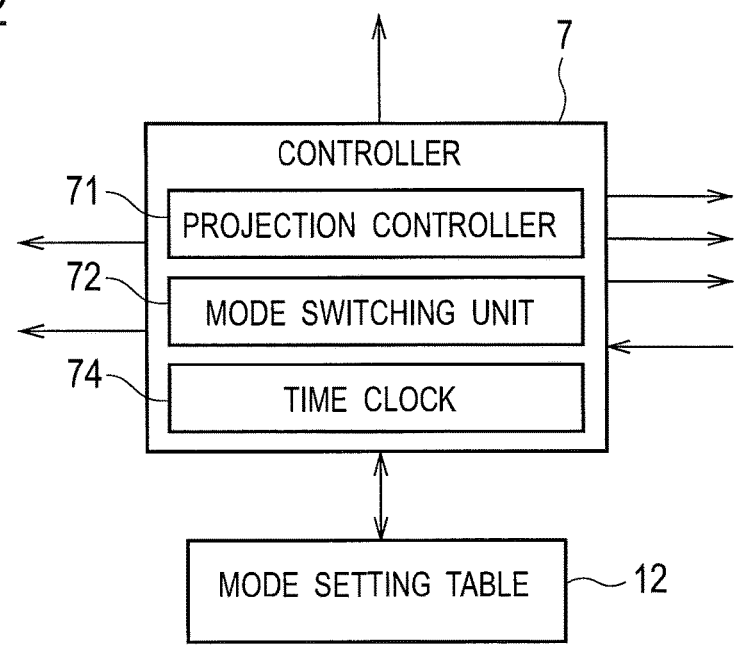
FIG. 22 is a partial block diagram showing a second modified example of the imaging device according to the embodiment.

As shown in FIG. 22, the normal mode, the intermediate mode, and the night-vision mode are set in a mode setting table 12 depending on the combination of the date and the time zone. A time clock 73 in the controller 7 manages the date and the time. The controller 7 refers to the date and the time indicated on the time clock 73 so as to read out the mode set in the mode setting table 12.

The projection controller 71 and the mode switching unit 72 control the imaging device so as to select the mode read from the mode setting table 12.

<Third Modified Example of Imaging Device>

Figure 23:
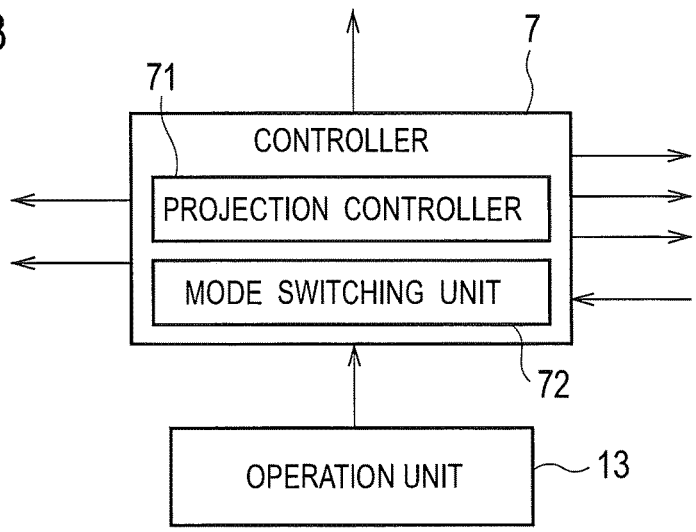
FIG. 23 is a partial block diagram showing a third modified example of the imaging device according to the embodiment.

As shown in FIG. 23, a user may control the imaging device with an operation unit 13 by manually selecting one of the modes, so as to set the projection controller 71 and the mode switching unit 72 to the selected mode. The operation unit 13 may be operated using the operation buttons provided on the casing of the imaging device or by a remote controller.

<Image Signal Processing Method>

The image signal processing method executed by the imaging device shown in FIG. 1 is again described with reference to FIG. 24.

Figure 24:
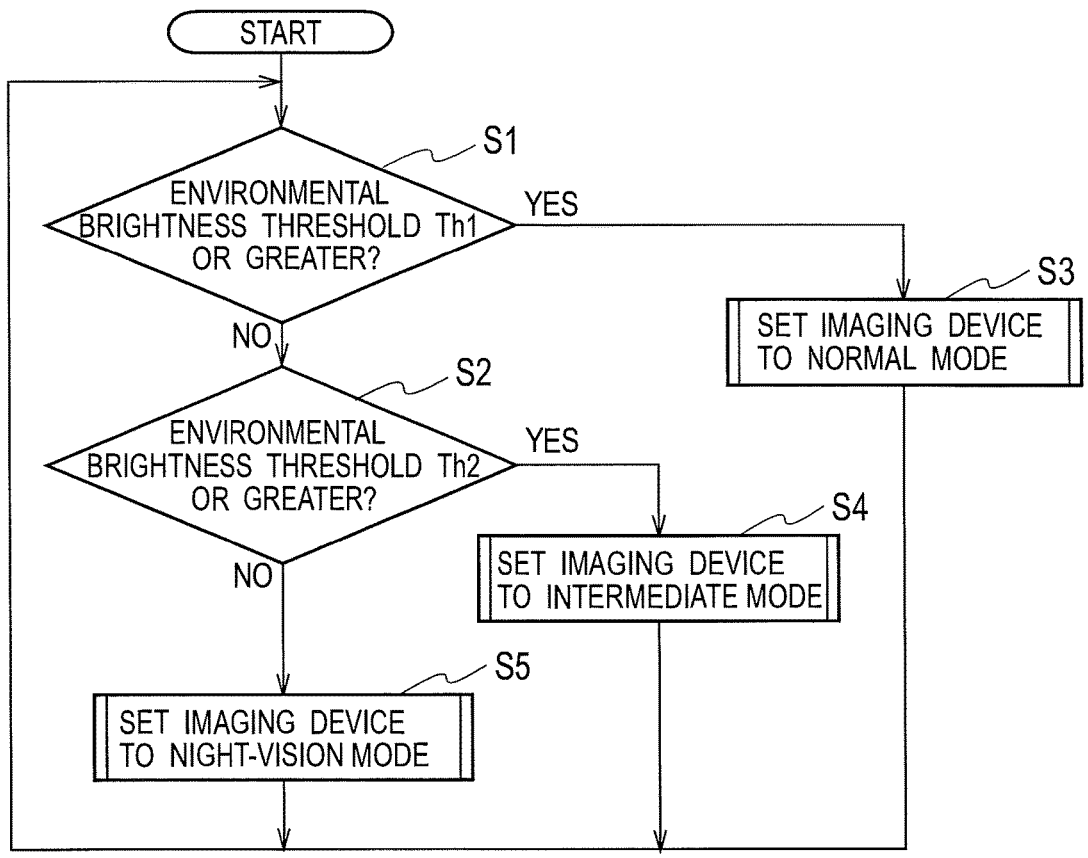
FIG. 24 is a flowchart showing an image signal processing method.

In FIG. 24, once the imaging device starts operating, the controller 7 determines in step S1 whether the environmental brightness is the threshold Th1 or greater. When the environmental brightness is the threshold Th1 or greater (YES), the controller 7 executes the processing in the normal mode in step S3. When the environmental brightness is not the threshold Th1 or greater (NO), the controller 7 determines in step S2 whether the environmental brightness is threshold Th2 or greater.

When the environmental brightness is the threshold Th2 or greater (YES), the controller 7 executes the processing in the intermediate mode in step S4. When the environmental brightness is not the threshold Th2 or greater (NO), the controller 7 executes the processing in the night-vision mode in step S5.

The controller 7 returns the processing to step S1 after executing the processing from steps S3 to S5, and repeats the respective following steps.

Figure 25:
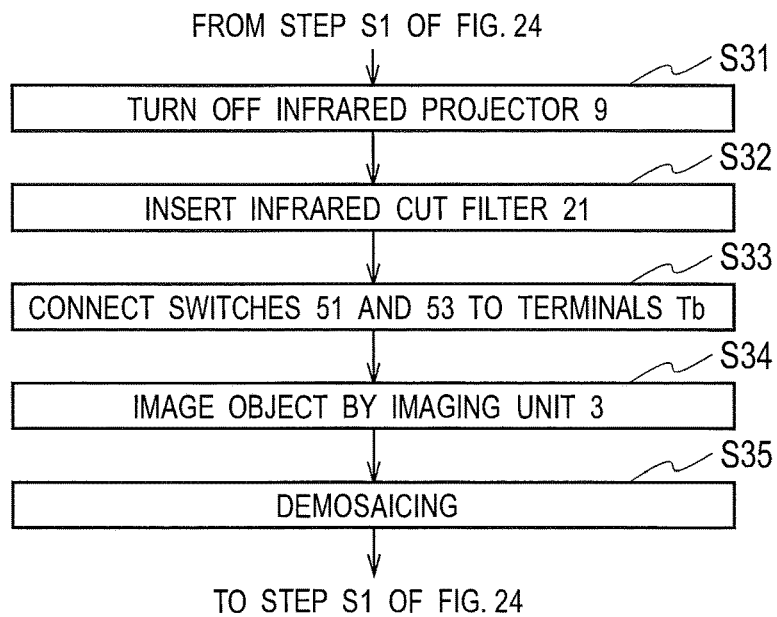
FIG. 25 is a flowchart showing specific processing steps in the normal mode shown in step S3 of FIG. 24.

FIG. 25 shows the specific processing in the normal mode in step S3. In FIG. 25, the controller 7 (the projection controller 71) turns off the infrared projector 9 in step S31. The controller 7 inserts the infrared cut filter 21 in step S32. The controller 7 (the mode switching unit 72) connects the switches 51 and 53 to the respective terminals Tb in step S33. The execution order from steps S31 to S33 is optional. The steps S31 to S33 can be executed simultaneously.

The controller 7 directs the imaging unit 3 to image an object in step S34. The controller 7 controls the image processing unit 5 in step S35 so that the demosaicing unit 54 subjects, to demosaicing, a frame composing image signals generated when the imaging unit 3 images the object.

Figure 26:
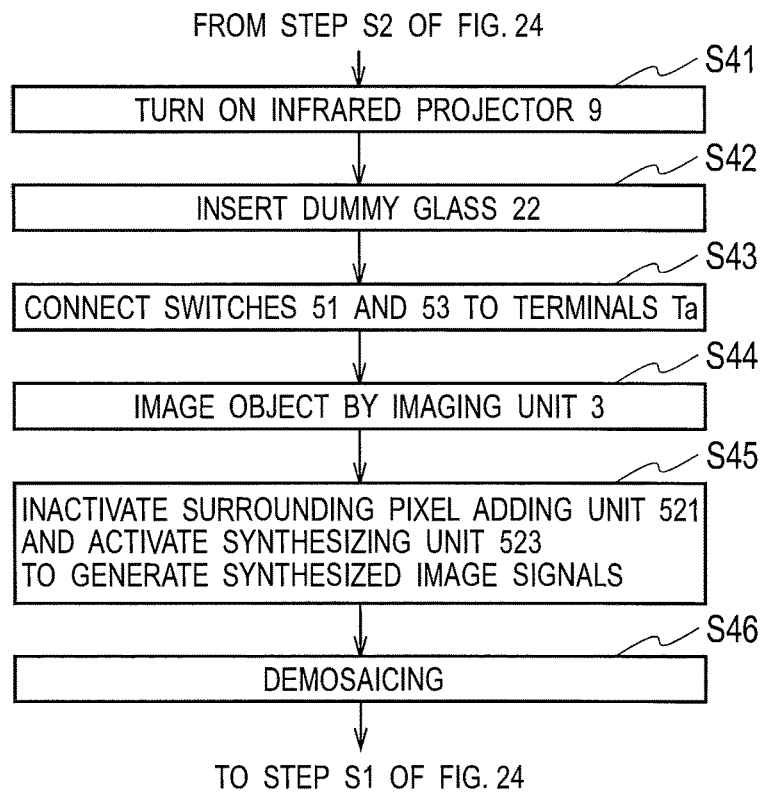
FIG. 26 is a flowchart showing specific processing steps in the intermediate mode shown in step S4 of FIG. 24.

FIG. 26 shows the specific processing in the intermediate mode in step S4. In FIG. 26, the controller 7 (the projection controller 71) turns on the infrared projector 9 in step S41 so that the projecting portions 91 to 93 project infrared light with the respective wavelengths IR1 to IR3 in a time division manner.

The controller 7 inserts the dummy glass 22 in step S42. The controller 7 (the mode switching unit 72) connects the switches 51 and 53 to the respective terminals Ta in step S43. The execution order from steps S41 to S43 is optional. The steps S41 to S43 may be executed simultaneously.

The controller 7 directs the imaging unit 3 to image an object in step S44. The imaging unit 3 images the object in a state where the infrared light with the wavelength IR1 assigned to R, the infrared light with the wavelength IR2 assigned to G, and the infrared light with the wavelength IR3 assigned to B, are each projected.

The controller 7 (the mode switching unit 72) controls the pre-signal processing unit 52 in step S45 so as to inactivate the surrounding pixel adding unit 521 and activate the synthesizing unit 523 to generate synthesized image signals.

The respective frames composing the image signals generated when the imaging unit 3 images the object in the state where the infrared light with the respective wavelengths IR1, IR2, and IR3 is projected, are defined as a first frame, a second frame, and a third frame.

The synthesizing unit 523 arranges the pixel data for the three primary colors based on the pixel data for R in the first frame, the pixel data for G in the second frame, and the pixel data for B in the third frame, so as to have the same array as the filter elements in the color filter 32. The synthesizing unit 523 thus generates the synthesized image signals in a manner such that the image signals in the first to third frames are synthesized in one frame.

The controller 7 controls the image processing unit 5 in step S46 so that the demosaicing unit 54 subjects the frame composing the synthesized image signals to demosaicing.

The demosaicing unit 54 executes, based on the frame of the synthesized image signals, demosaicing for generating an R frame, a G frame, and a B frame, so as to sequentially generate the frames of the three primary colors subjected to demosaicing.

The demosaicing unit 54 can generate the R frame by interpolating the pixel data for R in the pixel positions where no pixel data for R is present. The demosaicing unit 54 can generate the G frame by interpolating the pixel data for G in the pixel positions where no pixel data for G is present. The demosaicing unit 54 can generate the B frame by interpolating the pixel data for B in the pixel positions where no pixel data for B is present.

When executing the operations in the first intermediate mode, the controller 7 activates the same-position pixel adding unit 522 in step S45. When executing the operations in the second intermediate mode, the controller 7 inactivates the same-position pixel adding unit 522 in step S45.

Figure 27:
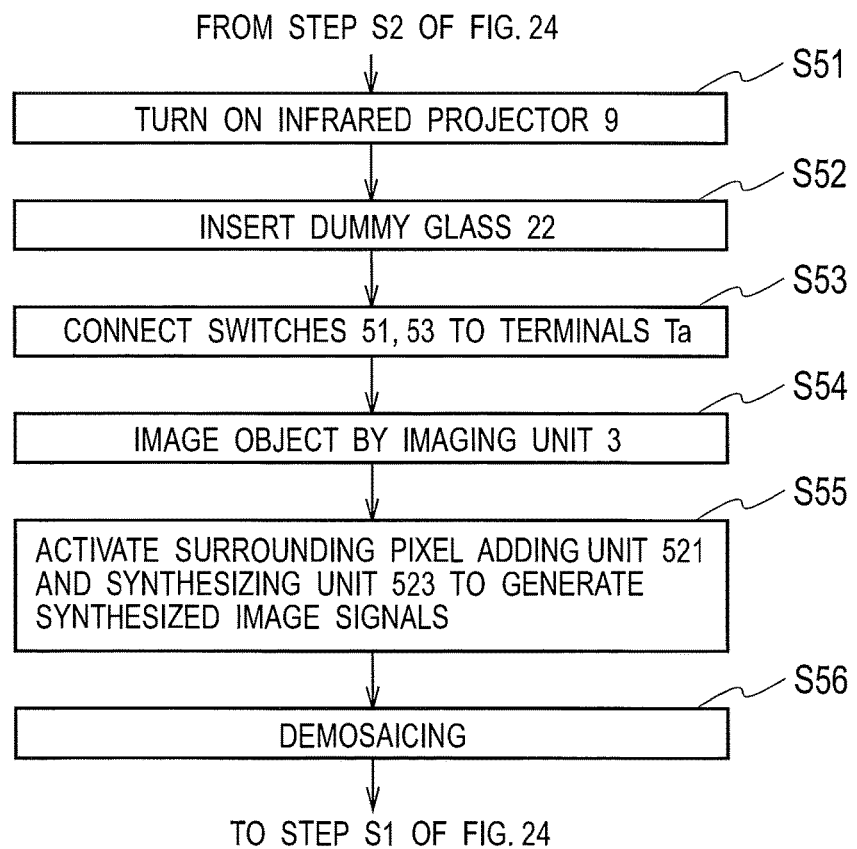
FIG. 27 is a flowchart showing specific processing steps in the night-vision mode shown in step S5 of FIG. 24.

FIG. 27 shows the specific processing in the night-vision mode in step S5. In FIG. 27, the controller 7 (the projection controller 71) turns on the infrared projector 9 in step S51 so that the projecting portions 91 to 93 project infrared light with the respective wavelengths IR1 to IR3 in a time division manner.

The controller 7 inserts the dummy glass 22 in step S52. The controller 7 (the mode switching unit 72) connects the switches 51 and 53 to the respective terminals Ta in step S53. The execution order from steps S51 to S53 is optional. The steps S51 to S53 may be executed simultaneously.

The controller 7 directs the imaging unit 3 to image an object in step S54. The controller 7 (the mode switching unit 72) controls the pre-signal processing unit 52 in step S55 so as to activate the surrounding pixel adding unit 521 and the synthesizing unit 523 to generate synthesized image signals.

The controller 7 controls the image processing unit 5 in step S56 so that the demosaicing unit 54 subjects the frame composing the synthesized image signals to demosaicing.

When executing the operations in the first night-vision mode, the controller 7 activates the same-position pixel adding unit 522 in step S55. When executing the operations in the second night-vision mode, the controller 7 inactivates the same-position pixel adding unit 522 in step S55.

<Image Signal Processing Program>

In FIG. 1, the controller 7 or the integrated portion of the image processing unit 5 and the controller 7 may be composed of a computer (microcomputer), and an image signal processing program (computer program) may be executed by the computer, so as to implement the same operations as those in the imaging device described above.

Figure 28:
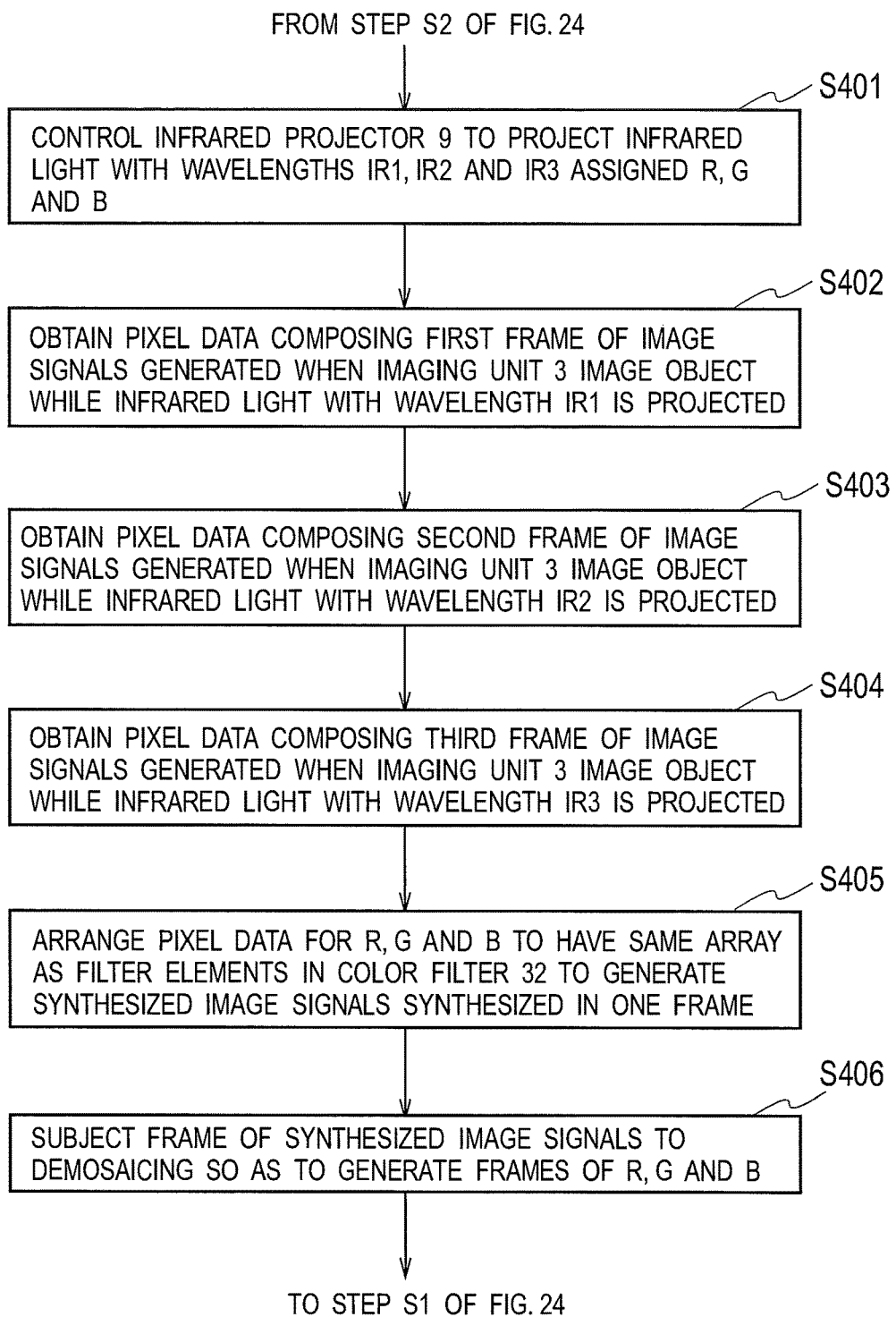
FIG. 28 is a flowchart showing processing steps executed by a computer directed by an image signal processing program.

An example of a procedure of the processing executed by the computer when the processing in the intermediate mode executed in step S4 shown in FIG. 24 is included in the image signal processing program, is described below with reference to FIG. 28. FIG. 28 shows the processing executed by the computer instructed by the image signal processing program.

In FIG. 28, the image signal processing program instructs the computer to control the infrared projector 9 in step S401 to project infrared light with the wavelengths IR1, IR2, and IR3 assigned to R, G, and B, respectively.

The step in step S401 may be executed by an external unit outside of the image signal processing program. In FIG. 28, the step of inserting the dummy glass 22 is omitted. The step of inserting the dummy glass 22 may be executed by the external unit outside of the image signal processing program.

The image signal processing program instructs the computer in step S402 to obtain the pixel data composing the first frame of the image signals generated when the imaging unit 3 images the object in the state where the infrared light with the wavelength IR1 is projected.

The image signal processing program instructs the computer in step S403 to obtain the pixel data composing the second frame of the image signals generated when the imaging unit 3 images the object in the state where the infrared light with the wavelength IR2 is projected.

The image signal processing program instructs the computer in step S404 to obtain the pixel data composing the third frame of the image signals generated when the imaging unit 3 images the object in the state where the infrared light with the wavelength IR3 is projected. The execution order from steps S402 to 404 is optional.

The image signal processing program instructs the computer in step S405 to arrange the respective pixel data for R, G, and B in such a manner as to have the same array as the filter elements in the color filter 32, so as to generate the synthesized image signals synthesized in one frame.

In the intermediate mode, the image signal processing program does not instruct the computer to execute the processing of adding the surrounding pixels in step S405.

The image signal processing program instructs the computer in step S406 to subject the frame of the synthesized image signals to demosaicing, so as to generate the frames of R, G, and B.

Although not illustrated in the drawing, the image signal processing program may instruct the computer to execute the processing of adding the surrounding pixels in step S405 shown in FIG. 28 when the processing in the night-vision mode executed in step S5 shown in FIG. 24 is included in the image signal processing program.

The image signal processing program may be a computer program stored in a storage medium readable on the computer. The image signal processing program may be provided in a state of being stored in the storage medium, or may be provided via a network such as the Internet in a manner such that the image signal processing program is downloaded to the computer. The storage medium readable on the computer may be an arbitrary non-transitory storage medium, such as CD-ROM and DVD-ROM.

<Reduction in Color Variation when Imaging Moving Object>

Next, variations in color and a method of reducing the variations in color are described below, the variations in color being caused when the imaging device according to the present embodiment images a moving object in the intermediate mode or the night-vision mode as described above.

Figure 29:
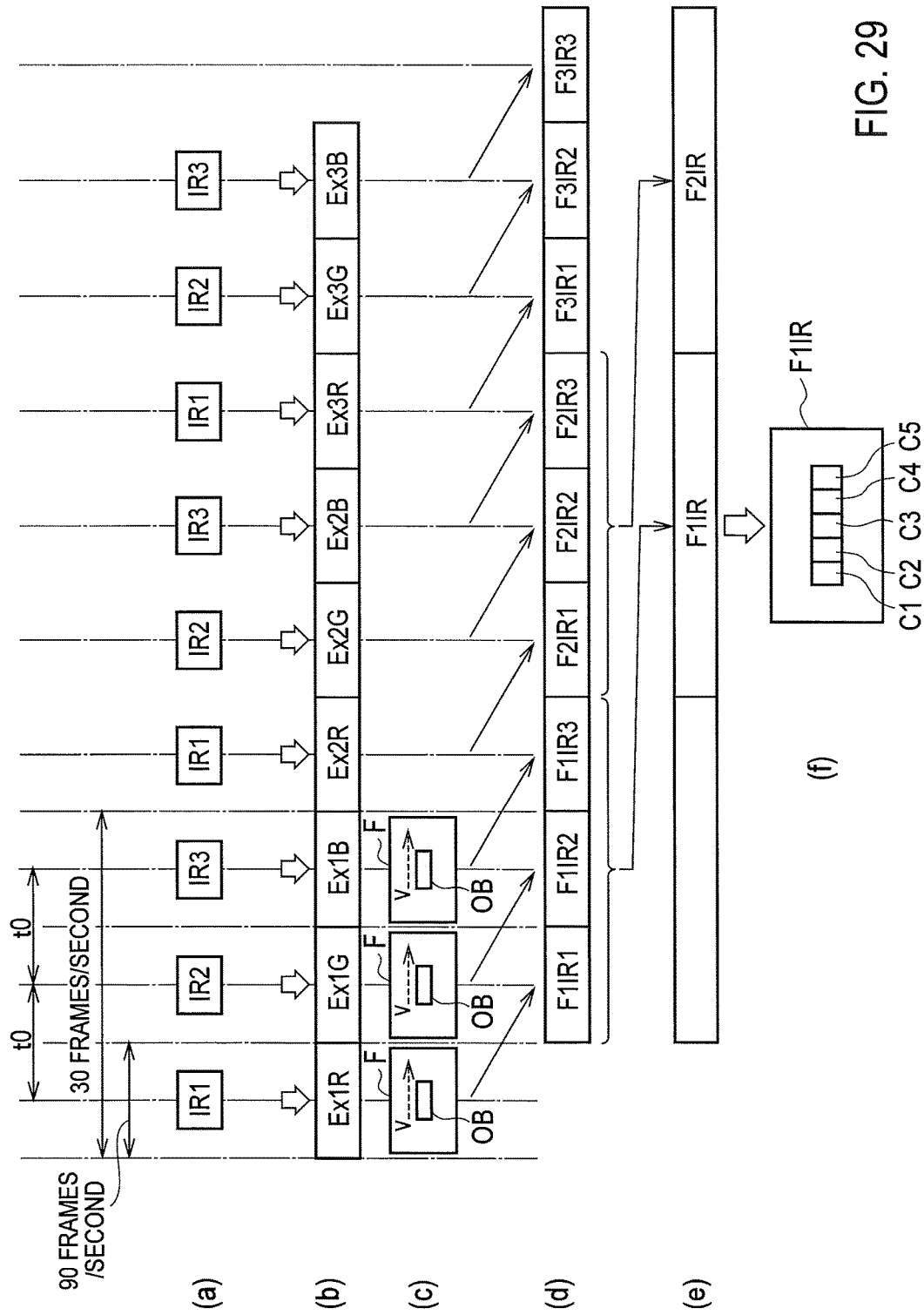
FIG. 29 is a timing chart schematically showing a method for controlling the imaging device when the imaging device generates a frame of an image signal while taking no account of variations in color.

FIG. 29 is a view schematically showing a method for controlling the imaging device when the imaging device generates a frame of an image signal, while taking no account of variations in color.

Item (a) of FIG. 29 is the same as item (a) of FIG. 8, showing a state where infrared light is projected from the infrared projector 9. FIG. 29 shows a case where the period in which the infrared light of each of the wavelengths IR1 to IR3 is projected is not the whole one frame period of the maximum exposure time, but is shorter than the one frame period.

As shown in item (b) of FIG. 29, the exposures Ex1R, Ex1G, Ex1B, Ex2R, Ex2G, Ex2B, etc., are each obtained at the point when the infrared light of each of the wavelengths IR1 to IR3 is projected.

Item (c) of FIG. 29 shows frames F of images imaged by the exposures shown in item (b) of FIG. 29. FIG. 29 only shows the frames F obtained by the exposures Ex1R, Ex1G, and Ex1B. As shown in the three frames F, the rectangular object OB is assumed to be moving at speed v from left to right in the horizontal direction.

As shown in item (d) of FIG. 29, the frames F1IR1, F1IR2, and F1IR3 are obtained based on the exposures Ex1R, Ex1G, and Ex1B. The frames F2IR1, F2IR2, and F2IR3 are obtained based on the exposures Ex2R, Ex2G, and Ex2B. The frames F3IR1, F3IR2, and F3IR3 are obtained based on the exposures Ex3R, Ex3G, and Ex3B.

The imaging signals shown in item (b) and the frames shown in item (d) each have a frame frequency of 90 frames per second. The set of exposures Ex1R, Ex1G and Ex1B, the set of exposures Ex2R, Ex2G and Ex2B, and the set of exposures Ex3R, Ex3G and Ex3B each have a frame frequency of 30 frames per second.

As shown in item (e) of FIG. 29, the frames F1IR, F1IR2, and F1IR3 are synthesized to generate the frame F1IR. The frames F2IR, F2IR2, and F2IR3 are synthesized to generate the frame F2IR. The frames R1IR and F2IR each have a frame frequency of 30 frames per second.

As shown in items (a) and (b) of FIG. 29, the middle point of the period in which the infrared light of each of the wavelengths IR1 to IR3 is projected corresponds to the middle point of the one frame period of the maximum exposure time.

Since the object OB is irradiated with the infrared light of the wavelength IR1 for generating the R signal during the exposure Ex1R, the object OB in the frame F1IR1 is indicated by red or an equivalent color. Since the object OB is irradiated with the infrared light of the wavelength IR2 for generating the G signal during the exposure Ex1G, the object OB in the frame F1IR2 is indicated by green or an equivalent color.

Since the object OB is irradiated with the infrared light of the wavelength IR3 for generating the B signal during the exposure Ex1B, the object OB in the frame F1IR3 is indicated by blue or an equivalent color.

In actual cases, sometimes the object OB cannot be indicated by the respective corresponding colors depending on the material of the object OB; however, for reasons of expediency, it is assumed that the object OB in the frame F1IR1 is indicated by red, the object OB in the frame F1IR2 is indicated by green, and the object OB in the frame F1IR3 is indicated by blue.

The interval between the middle points of the respective maximum exposure times shown in item (b) of FIG. 29 is defined as time t0. The object OB moves a distance [ΔLrg=v×t0] between the frames F1IR1 and F1IR2. Therefore, as shown in item (f) of FIG. 29, the frame F1IR is provided with the color-shift region C1 indicated by red, and having a length corresponding to the distance ΔLrg.

The frame F1IR, adjacent to the color-shift region C1, is provided with the color-shift region C2 indicated by yellow caused such that the object OB in red in the frame F1IR1 is superimposed on the object OB in green in the frame F1IR2. Note that the color-shift region C2 does not necessarily result in actual yellow, but is assumed to have yellow for reasons of expediency.

The frame F1IR, adjacent to the color-shift region C2, is provided with the region C3 indicated by a proper color, obtained such that the objects OB in the respective frames F1IR1, F1IR2, and F1IR3 are all superimposed together.

The frame F1IR, adjacent to the region C3, is provided with the color-shift region C4 indicated by cyan caused such that the object OB in green in the frame F1IR2 is superimposed on the object OB in blue in the frame F1IR3. Note that the color-shift region C4 does not necessarily result in actual cyan, but is assumed to have cyan for reasons of expediency.

The object OB moves by a distance [ΔLgb=v×t0] between the frames F1IR2 and F1IR3. Therefore, the frame F1IR, adjacent to the color-shift region C4, is provided with the color-shift region C5 indicated by blue and having a length corresponding to the distance ΔLgb.

As described above, when the object OB is a moving object, the color-shift regions C1, C2, C4, and C5 are caused around the region C3 indicated by the proper color, which leads to a deterioration of the image quality.

Figure 30:
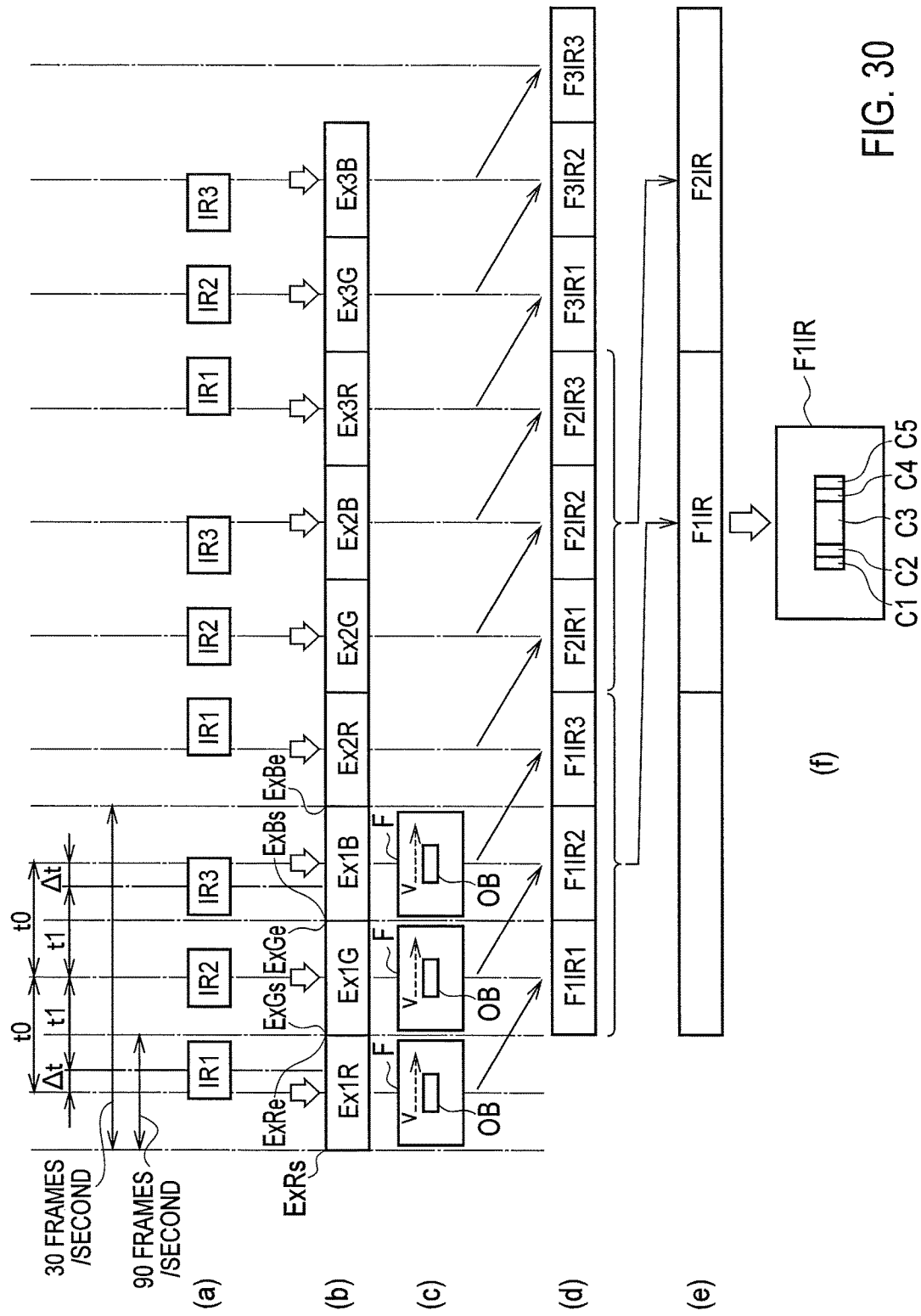
FIG. 30 is a timing chart schematically showing a first example of a method for controlling the imaging device that can minimize variations in color when generating a frame of an image signal.
Figure 31:
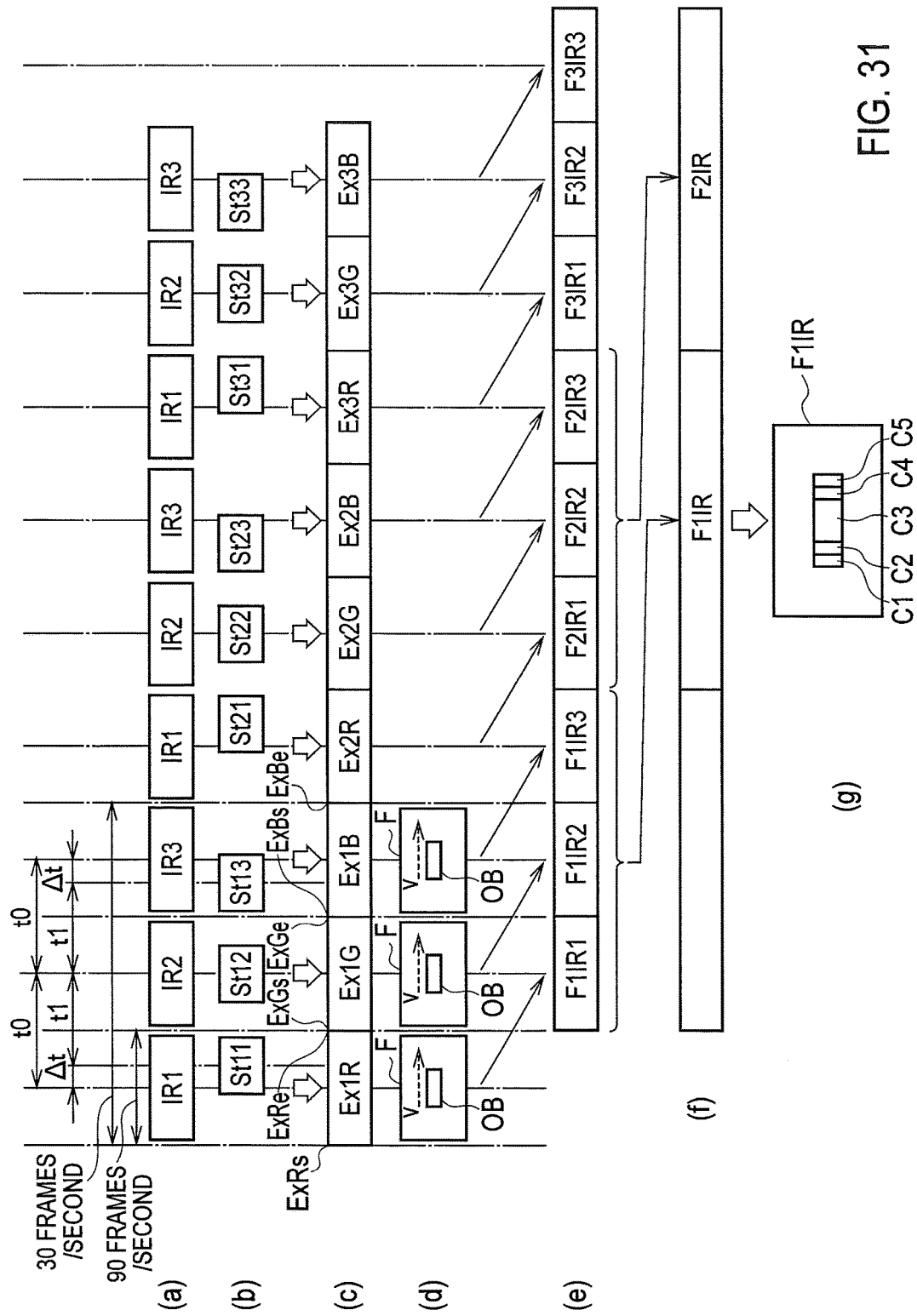
FIG. 31 is a timing chart schematically showing a second example of the method for controlling the imaging device that can minimize variations in color when generating a frame of an image signal.
Figure 32:
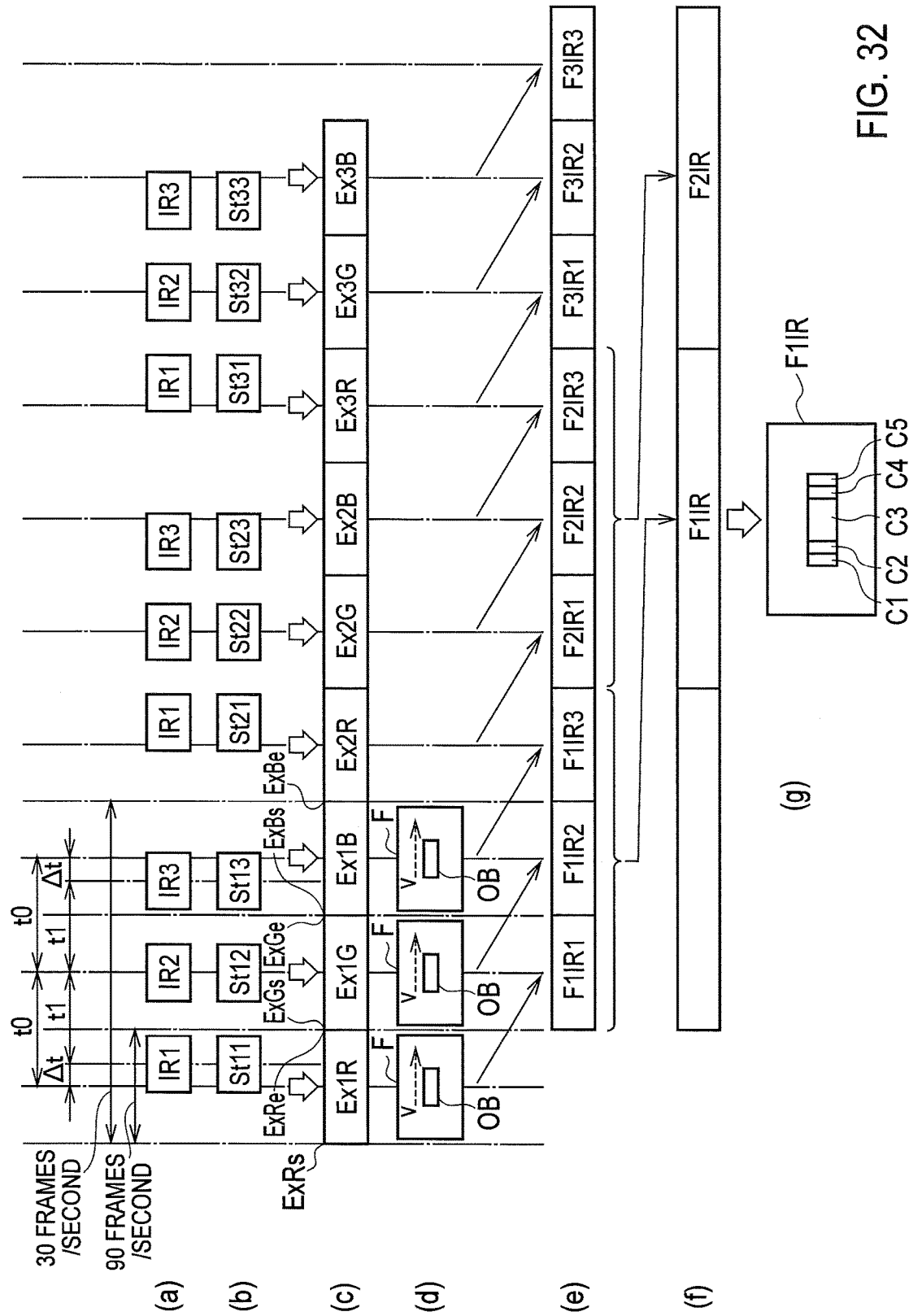
FIG. 32 is a timing chart schematically showing a third example of the method for controlling the imaging device that can minimize variations in color when generating a frame of an image signal.

FIGS. 30 to 32 show the preferred method for controlling the imaging device in order to minimize variations in color when imaging the object OB, which is moving. The respective controlling methods shown in FIGS. 30 to 32 are described below in order.

Item (b) of FIG. 30 shows exposure-start timing ExRs and exposure-end timing ExRe for the exposure Ex1R, exposure-start timing ExGs and exposure-end timing ExGe for the exposure Ex1G, and exposure-start timing ExBs and exposure-end timing ExBe for the exposure Ex1B.

FIG. 30 shows a first example of the controlling method. As shown in item (a) of FIG. 30, the middle point of the period in which the infrared light of the wavelength IR1 is projected is shifted forward toward the exposure-end timing ExRe, from the middle point of the maximum exposure time of the exposure Ex1R.

The middle point of the period in which the infrared light of the wavelength IR3 is projected is shifted backward toward the exposure-start timing ExBs from the middle point of the maximum exposure time of the exposure Ex1B.

The middle point of the period in which the infrared light of the wavelength IR2 is projected corresponds to the middle point of the maximum exposure time of the exposure Ex1G, as in the case of item (a) of FIG. 29.

The middle point of the period in which the infrared light of the wavelength IR2 is projected does not necessarily correspond to the middle point of the maximum exposure time of the exposure Ex1G; however, these middle points preferably correspond to each other.

The timing of projecting the infrared light of the wavelengths IR1 to IR3 with respect to the exposures Ex2R, Ex2G, and Ex2B, the exposures Ex3R, Ex3G, and Ex3B, etc., is the same as the timing of projecting the infrared light of the wavelengths IR1 to IR3 with respect to the exposures Ex1R, Ex1G, and Ex1B.

The interval between the middle point of the period in which the infrared light of the wavelength IR2 is projected, and the middle point of the period in which the infrared light of the wavelength IR1 is projected, is defined as time t1. The interval between the middle point of the period in which the infrared light of the wavelength IR2 is projected, and the middle point of the period in which the infrared light of the wavelength IR3 is projected, is defined as time t1.

The time t1 is shorter than the time t0 by Δt. Therefore, the distance that the object OB moves between the frames F1IR1 and F1IR2 is reduced by ΔL=v×Δt. The distance that the object OB moves between the frames F1IR2 and F1IR3 is also reduced by ΔL=v×Δt.

Accordingly, as shown in item (f) of FIG. 30, each length of the color-shift regions C1, C2, C4, and C5 is reduced by ΔL. This increases the length of the region C3 indicated by the proper color and leads to a reduction in color variation.

In the first example, the middle point of the period in which the infrared light of the wavelength IR1 is projected is shifted toward the exposure-end timing ExRe, and the middle point of the period in which the infrared light of the wavelength IR3 is projected is shifted toward the exposure-start timing ExBs.

When only the middle point of the period in which the infrared light of the wavelength IR1 is projected is shifted toward the exposure-end timing ExRe, the color-shift regions C1 and C2 can be decreased. When only the middle point of the period in which the infrared light of the wavelength IR3 is projected is shifted toward the exposure-start timing ExBs, the color-shift regions C4 and C5 can be decreased.

In the first example, as described above, the interval between the middle point of the period of the infrared light projected in the middle, and the middle point of the period of the infrared light projected before or after the middle infrared light, is shorter than the interval between the middle point of the period of the infrared light projected in the middle, and the middle point of the maximum exposure time of the exposure Ex1R or Ex1B. Thus, the first example can minimize variations in color.

The configurations of the imaging device controlled by the controlling method of the first example are summarized as follows. The first infrared light, the second infrared light, and the third infrared light are sequentially projected. The first infrared light has the first wavelength assigned to the first color of red, green, and blue. The second infrared light has the second wavelength assigned to the second color of red, green, and blue. The third infrared light has the third wavelength assigned to the third color of red, green, and blue.

The projection controller 71 controls the infrared projector 9 to sequentially project the first infrared light, the second infrared light, and the third infrared light.

The imaging unit 3 images an object in a state where the first infrared light is projected in at least part of one frame period so as to generate the first frame based on the first imaging signal. The one frame period is determined depending on the maximum exposure time in the imaging unit 3.

The imaging unit 3 images the object in a state where the second infrared light is projected in at least part of the one frame period so as to generate the second frame based on the second imaging signal. The imaging unit 3 images the object in a state where the third infrared light is projected in at least part of the one frame period so as to generate the third frame based on the third imaging signal.

The image processing unit 5 synthesizes the first to third frames to generate a frame of an image signal.

The middle point of the period in which the second infrared light is projected is defined as the first timing. The middle point of the period in which the first or third infrared light is projected is defined as the second timing. The middle point of the one frame period of the first or third frame is defined as the third timing.

The projection controller 71 sets the interval between the first timing and the second timing shorter than the interval between the first timing and the third timing, and controls the infrared projector 9 to project the first to third infrared lights.

The middle point of the one frame period of the second frame is defined as the fourth timing. It is particularly preferable that the projection controller 71 control the infrared projector 9 to project the second infrared light by conforming the first timing to the fourth timing.

A control program (computer program) of the imaging device may be executed by a computer so as to implement the operations of the imaging device controlled by the controlling method of the first example as described above. The control program of the imaging device may be a computer program stored in a non-transitory storage medium readable on a computer, as in the case of the image signal processing program described above.

More particularly, the control program of the imaging device is executed by the computer to implement the first step of controlling the infrared projector 9 to project the first infrared light and the second step of generating the first frame. The control program of the imaging device is executed by the computer to implement the third step of controlling the infrared projector 9 to project the second infrared light and the fourth step of generating the second frame.

The control program of the imaging device is executed by the computer to implement the fifth step of controlling the infrared projector 9 to project the third infrared light, the sixth step of generating the third frame, and the seventh step of synthesizing the first to third frames to generate a frame of an image signal.

The control program of the imaging device sets the interval between the first timing and the second timing shorter than the interval between the first timing and the third timing.

A second example of the controlling method shown in FIG. 31 is described below, mainly with regard to the differences between this example and the first example shown in FIG. 30. Items (a) and (c) to (g) of FIG. 31 are the same as items (a) to (f) of FIG. 30.

In the second example, as shown in item (a) of FIG. 31, the infrared light having each of the wavelengths IR1 to IR3 is projected approximately during the whole one frame period of the respective exposures Ex1R, Ex1G, Ex1B, Ex2R, Ex2G, Ex2B, Ex3R, Ex3G, Ex3B, etc.

Item (b) of FIG. 31 shows the period and timing in which the electronic shutter of the imaging unit 3 is released, according to the control by the electronic shutter controller 73. In the frame period of the exposure Ex1G, the middle point of electronic shutter-release period St12 corresponds to the middle point of the maximum exposure time of the exposure Ex1G.

In the frame period of the exposure Ex1R, the middle point of electronic shutter-release period St11 is shifted forward toward the exposure-end timing ExRe from the middle point of the maximum exposure time of the exposure Ex1R. In the frame period of the exposure Ex1B, the middle point of electronic shutter-release period St13 is shifted backward toward the exposure-start timing ExBs from the middle point of the maximum exposure time of the exposure Ex1B.

The timing of the electronic shutter-release periods St21, St22, and St23, the electronic shutter-release periods St31, St32, and St33, etc., with respect to the exposures Ex2R, Ex2G, and Ex2B, the exposures Ex3R, Ex3G, and Ex3B, etc., respectively, is the same as the timing of the electronic shutter-release periods St11, St12, and St13 with respect to the exposures Ex1R, Ex1G, and Ex1B.

Even when the infrared light is projected during the whole one frame period of each exposure, the imaging signal obtained by imaging the object OB irradiated with the infrared light is input into the A/D converter only for the electronic shutter-release period.

The second example can therefore obtain the frame F1IR, including the region C3 indicated by the proper color and the color-shift regions C1, C2, C4, and C5, as shown in item (g) of FIG. 31, as in the case of the frame F1IR shown in item (f) of FIG. 30. Accordingly, the second example can also minimize variations in color.

A third example of the controlling method shown in FIG. 32 is described below, mainly with regard to the differences between this example, the first example shown in FIG. 30, and the second example shown in FIG. 31. Items (a) to (g) of FIG. 32 correspond to items (a) to (g) of FIG. 31, respectively.

In the third example, as shown in items (a) and (b) of FIG. 32, the period in which the infrared light with the wavelengths IR1 to IR3 is projected corresponds to each electronic shutter-release period. The period and timing in which the infrared light having the respective wavelengths IR1 to IR3 is projected in the third example are the same as those in the first example shown in FIG. 30.

The third example differs from the first example in that each electronic shutter-release period corresponds to the period in which the infrared light is projected. The third example can also minimize variations in color.

The configurations of the imaging device controlled by the controlling method of the second or third example are summarized as follows, which are different from those of the first example.

The electronic shutter controller 73 controls the functions of the electronic shutter in the imaging unit 3. The middle point of the period in which the imaging unit 3 is exposed while the second infrared light is projected is defined as the first timing. The middle point of the period in which the imaging unit 3 is exposed while the first or third infrared light is projected is defined as the second timing. The middle point of the one frame period of the first or third frame is defined as the third timing.

The electronic shutter controller 73 controls the period and timing in which the imaging unit 3 is exposed such that the interval between the first timing and the second timing is set shorter than the interval between the first timing and the third timing.

The control program (computer program) of the imaging device may be executed by the computer so as to implement the operations of the imaging device controlled by the controlling method of the second or third example as described above.

The control program of the imaging device can therefore be executed by the computer, by use of the functions of the electronic shutter in the imaging unit 3, to implement processing to control the period and timing in which the imaging unit 3 is exposed such that the interval between the first timing and the second timing is set shorter than the interval between the first timing and the third timing.

The present invention is not limited to the embodiments described above, and various modifications and improvements can be made without departing from the scope of the present invention. The controller 7 and the image processing unit 5 may be composed of one or more hardware components (circuits or processors). The use of hardware or software is optional. The imaging device may only include hardware, or part of the imaging device may be composed of software.

What is claimed is:

1. An imaging device comprising:
 a projection controller configured to control an infrared projector to selectively and sequentially project in the following order, a first infrared light having a first wavelength assigned to a first color of red, green, and blue, a second infrared light having a second wavelength assigned to a second color of red, green, and blue, and a third infrared light having a third wavelength assigned to a third color of red, green, and blue, the first, second and third wavelengths being 700 nm or greater;
 an imaging unit configured to image an object in a state where the first infrared light is projected in at least part of one frame period so as to generate a first frame based on a first imaging signal, to image the object in a state where the second infrared light is projected in at least part of the one frame period so as to generate a second frame based on a second imaging signal, and to image the object in a state where the third infrared light is projected in at least part of the one frame period so as to generate a third frame based on a third imaging signal, the first, second, and third frames being generated in this order;
 an electronic shutter controller configured to control a function of an electronic shutter in the imaging unit; and
 an image processing unit configured to synthesize the first to third frames to generate a frame of an image signal,
 wherein the electronic shutter controller controls a period and timing in which the imaging unit is exposed such that an interval between a first timing and a second timing is set shorter than an interval between the first timing and a third timing,
 wherein the first timing is a middle point of a period in which the imaging unit is exposed in the state where the second infrared light is projected, the second timing is a middle point of a period in which the imaging unit is exposed in the state where the first or third infrared light is projected, and the third timing is a middle point of the one frame period of the first or third frame,
 and wherein when the second timing is the middle point of the period in which the imaging unit is exposed in the state where the first infrared light is projected, the third timing is the middle point of the one frame period of the first frame, and when the second timing is the middle point of the period in which the imagining unit is exposed in the state where the third infrared light is projected, the third timing is the middle point of the one frame period of third frame.

2. The imaging device according to claim 1, wherein the electronic shutter controller controls the period and timing in which the imaging unit is exposed such that the first timing corresponds to a fourth timing that is a middle point of the one frame period of the second frame.

3. A method for controlling an imaging device, comprising:
 a first step of imaging an object by an imaging unit in a state where a first infrared light having a first wavelength assigned to a first color of red, green, and blue is projected in at least part of one frame period so as to generate a first frame based on a first imaging signal, the first wavelength being 700 nm or greater;

a second step, implemented after the first step, of imaging the object by the imaging unit in a state where a second infrared light having a second wavelength assigned to a second color of red, green, and blue is projected in at least part of the one frame period so as to generate a second frame based on a second imaging signal, the second wavelength being 700 nm or greater;

a third step, implemented after the second step, of imaging the object by the imaging unit in a state where a third infrared light having a third wavelength assigned to a third color of red, green, and blue is projected in at least part of the one frame period so as to generate a third frame based on a third imaging signal, the third wavelength being 700 nm or greater; and a fourth step of synthesizing the first to third frames to generate a frame of an image signal, wherein, in the first to third steps, a period and timing in which the imaging unit is exposed in a state where the first to third infrared lights are each projected, are determined by use of a function of an electronic shutter in the imaging unit, wherein an interval between a first timing and a second timing is set shorter than an interval between the first timing and a third timing, the first timing being a middle point of a period in which the imaging unit is exposed in the state where the second infrared light is projected, the second timing being a middle point of a period in which the imaging unit is exposed in the state where the first or third infrared light is projected, and the third timing being a middle point of the one frame period of the first or third frame, and wherein when the second timing is the middle point of the period in which the imaging unit is exposed in the state where the first infrared light is projected, the third timing is the middle point of the one frame period of the first frame, and when the second timing is the middle point of the period in which the imaging unit is exposed in the state where the third infrared light is projected, the third timing is the middle point of the one frame period of third frame.

4. A control program of an imaging device executed by a computer and stored in a non-transitory storage medium to implement the following steps, comprising:

a first step of controlling an infrared projector to project a first infrared light having a first wavelength assigned to a first color of red, green, and blue, the first wavelength being 700 nm or greater;

a second step of imaging an object by an imaging unit in a state where the first infrared light is projected in at least part of one frame period so as to generate a first frame based on a first imaging signal;

a third step, continued from the first step, of controlling the infrared projector to project a second infrared light having a second wavelength assigned to a second color of red, green, and blue, the second wavelength being 700 nm or greater;

a fourth step of imaging the object by the imaging unit in a state where the second infrared light is projected in at least part of the one frame period so as to generate a second frame based on a second imaging signal;

a fifth step, continued from the third step, of controlling the infrared projector to project a third infrared light having a third wavelength assigned to a third color of red, green, and blue;

a sixth step of imaging the object by the imaging unit in a state where the third infrared light is projected in at least part of the one frame period so as to generate a third frame based on a third imaging signal; and a seventh step of synthesizing the first to third frames to generate a frame of an image signal, wherein, in the second, fourth, and sixth steps, the control program implements processing to control a period and timing in which the imaging unit is exposed by use of a function of an electronic shutter in the imaging unit such that an interval between a first timing and a second timing is set shorter than an interval between the first timing and a third timing, wherein the first timing is a middle point of a period in which the imaging unit is exposed in the state where the second infrared light is projected, the second timing is a middle point of a period in which the imaging unit is exposed in the state where the first or third infrared light is projected, and the third timing is a middle point of the one frame period of the first or third frame, and wherein when the second timing is the middle point of the period in which the imaging unit is exposed in the state where the first infrared light is projected, the third timing is the middle point of the one frame period of the first frame, and when the second timing is the middle point of the period in which the imaging unit is exposed in the state where the third infrared light is projected, the third timing is the middle point of the one frame period of third frame.

* * * * *